(12) United States Patent
Sundaram et al.

(10) Patent No.: US 9,786,148 B2
(45) Date of Patent: Oct. 10, 2017

(54) DEVICES, SYSTEMS, AND METHODS FOR HEALTH MONITORING USING CIRCUMFERENTIAL CHANGES OF A BODY PORTION

(71) Applicant: Plethy, Inc., Los Gatos, CA (US)

(72) Inventors: Raja Sundaram, Los Gatos, CA (US); Paul Chirico, Campbell, CA (US); Bohdan Chopko, Henderson, NV (US); Samuel Linton, Sunnyvale, CA (US); John Kraczkowsky, Los Altos Hills, CA (US)

(73) Assignee: Plethy, Inc., Los Gatos, CA (US)

( * ) Notice: Subject to any disclaimer, the term of this patent is extended or adjusted under 35 U.S.C. 154(b) by 0 days.

(21) Appl. No.: 15/359,635

(22) Filed: Nov. 23, 2016

(65) Prior Publication Data

US 2017/0213437 A1 Jul. 27, 2017

Related U.S. Application Data

(63) Continuation of application No. PCT/US2016/063419, filed on Nov. 22, 2016.
(Continued)

(51) Int. Cl.
*G08B 13/18* (2006.01)
*G08B 21/04* (2006.01)
(Continued)

(52) U.S. Cl.
CPC ..... *G08B 21/0453* (2013.01); *G06F 19/3418* (2013.01); *H04W 84/18* (2013.01)

(58) Field of Classification Search
CPC ... G06F 19/321; A61B 5/1112; A61B 5/0022; A61B 5/002; G08B 21/0423; G08B 21/0453; G08B 21/0492; G08B 25/016
(Continued)

(56) References Cited

U.S. PATENT DOCUMENTS

| 5,497,787 A | 3/1996 | Nemesdy et al. |
| 5,991,654 A | 11/1999 | Tumey et al. |

(Continued)

FOREIGN PATENT DOCUMENTS

| WO | 9300042 A | 1/1993 |
| WO | 2005067796 A1 | 7/2005 |

(Continued)

OTHER PUBLICATIONS

International Search Report dated Mar. 24, 2017 from International Application PCT/US2016/63419, 3 pgs.
(Continued)

*Primary Examiner* — George Bugg
*Assistant Examiner* — Munear Akki
(74) *Attorney, Agent, or Firm* — Aurora Consulting LLC

(57) ABSTRACT

Devices, systems, and methods for monitoring health parameters of an individual, including circumferential changes to a portion of the individual's body, are provided herein. A monitoring device includes: a stretchable component configured to fit securely around a body portion, and a sensor module coupled thereto. The sensor module is configured to obtain and transmit a circumference measurement of the body portion. The sensor module may be further configured to obtain and transmit measurements of one or more additional parameters. A related monitoring system includes the described monitoring device and a mobile computing device. The mobile computing device is configured, at least in part, to: process the circumference measurements to identify and analyze any change in circumference of the body portion, and generate a relevant alert output. Methods performed by the various devices and systems are also provided.

29 Claims, 15 Drawing Sheets

Related U.S. Application Data

(60) Provisional application No. 62/281,600, filed on Jan. 21, 2016.

(51) Int. Cl.
*H04W 84/18* (2009.01)
*G06F 19/00* (2011.01)

(58) Field of Classification Search
USPC .............. 340/573.1, 539.12, 539.26, 825.56; 600/300, 301, 549
See application file for complete search history.

(56) References Cited

U.S. PATENT DOCUMENTS

| | | | |
|---|---|---|---|
| 6,047,203 A | 4/2000 | Sackner et al. | |
| 6,381,482 B1 | 4/2002 | Jayaraman et al. | |
| 6,941,775 B2 | 9/2005 | Sharma | |
| 6,980,853 B2 | 12/2005 | Miyoshi et al. | |
| 7,191,803 B2 | 3/2007 | Orr et al. | |
| 7,319,895 B2 | 1/2008 | Klefstad-Sillonville et al. | |
| 7,474,910 B2 | 1/2009 | Hassonjee et al. | |
| 7,559,902 B2 | 7/2009 | Ting et al. | |
| 7,849,888 B2 | 12/2010 | Karayianni et al. | |
| 8,146,171 B2 | 4/2012 | Chung et al. | |
| 8,403,881 B2 | 3/2013 | Ferren et al. | |
| 8,409,132 B2 | 4/2013 | Ferren et al. | |
| 8,551,008 B2 | 10/2013 | Naghavi et al. | |
| 8,585,602 B2 | 11/2013 | Crabtree et al. | |
| 8,597,194 B2 | 12/2013 | Barak | |
| 8,636,670 B2 | 1/2014 | Ferren et al. | |
| 8,870,813 B2 | 10/2014 | Ferren et al. | |
| 8,925,392 B2 | 1/2015 | Esposito et al. | |
| 9,186,092 B2 | 11/2015 | Mestrovic et al. | |
| 9,459,089 B2 | 10/2016 | Ganton et al. | |
| 2005/0059903 A1 | 3/2005 | Izumi | |
| 2007/0225614 A1* | 9/2007 | Naghavi | A61B 5/01 600/549 |
| 2009/0079559 A1 | 3/2009 | Dishongh et al. | |
| 2009/0234262 A1* | 9/2009 | Reid, Jr. | A61B 5/026 601/152 |
| 2009/0309579 A1* | 12/2009 | Cochran | A61B 5/1126 324/207.16 |
| 2010/0137701 A1 | 6/2010 | Papastefanou | |
| 2010/0240967 A1 | 9/2010 | Kim et al. | |
| 2010/0292549 A1* | 11/2010 | Shuler | A61B 5/0215 600/324 |
| 2011/0060252 A1* | 3/2011 | Simonsen | A61B 5/0488 600/595 |
| 2012/0065561 A1* | 3/2012 | Ballas | A61H 9/0021 601/152 |
| 2012/0173319 A1* | 7/2012 | Ferrara | G06Q 30/0241 705/14.4 |
| 2012/0179020 A1 | 7/2012 | Wekell | |
| 2014/0088461 A1* | 3/2014 | Mack | A43D 1/025 600/595 |
| 2014/0257836 A1 | 9/2014 | Walker et al. | |
| 2015/0351698 A1* | 12/2015 | Cronin | A61B 5/0022 600/485 |
| 2016/0015297 A1 | 1/2016 | Strauss et al. | |
| 2016/0232322 A1* | 8/2016 | Mensinger | G06F 19/3418 |
| 2016/0242646 A1* | 8/2016 | Obma | A61B 5/0024 |
| 2016/0278642 A1 | 9/2016 | Vogel et al. | |
| 2016/0302721 A1 | 10/2016 | Wiedenhoefer et al. | |
| 2016/0367406 A1* | 12/2016 | Barnett | A61B 5/48 |

FOREIGN PATENT DOCUMENTS

| | | |
|---|---|---|
| WO | 2009125327 A1 | 10/2009 |
| WO | 2013030709 A2 | 3/2013 |
| WO | 2014207653 A1 | 12/2014 |

OTHER PUBLICATIONS

Written Opinion dated Mar. 24, 2017 from International Application PCT/US2016/63419, 10 pgs.

\* cited by examiner

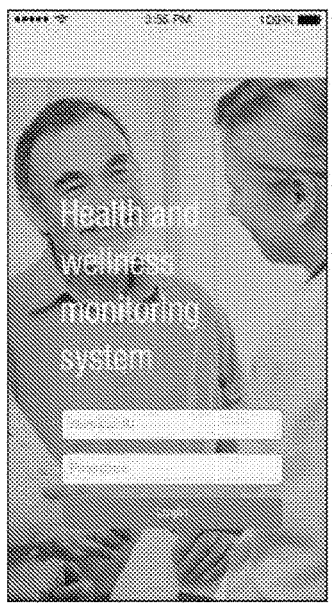 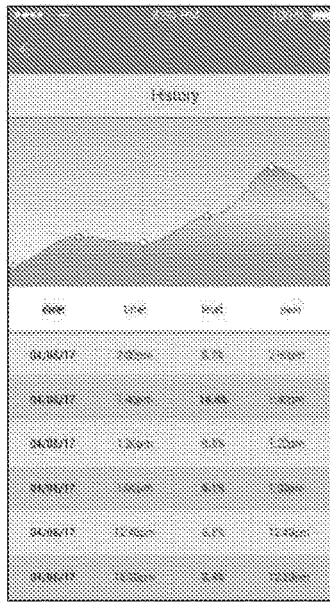 
FIG. 7A  FIG. 7B  FIG. 7C
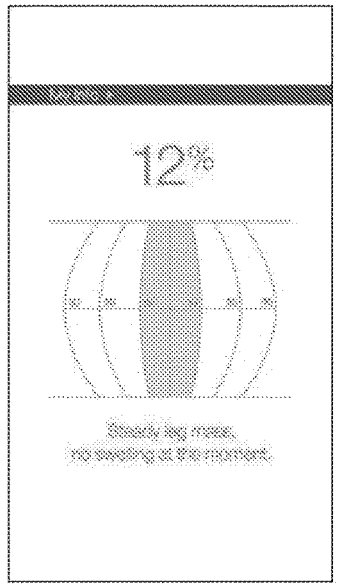 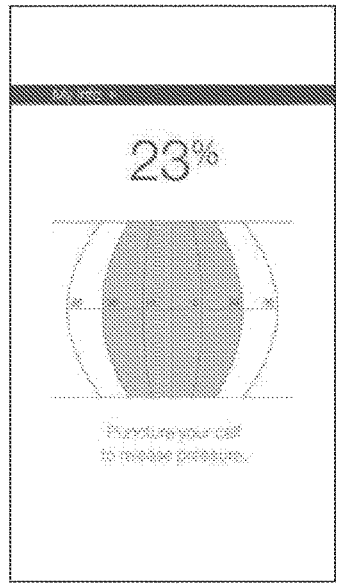 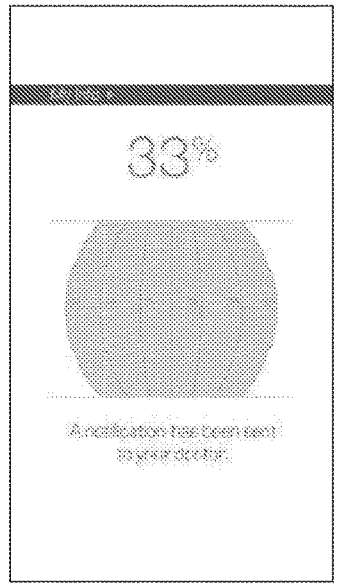
FIG. 7D  FIG. 7E  FIG. 7F

DEVICES, SYSTEMS, AND METHODS FOR HEALTH MONITORING USING CIRCUMFERENTIAL CHANGES OF A BODY PORTION

CROSS-REFERENCE TO RELATED APPLICATIONS

This application is a continuation of Patent Application No. PCT/US2016/063419, entitled "Devices, Systems, and Methods for Health Monitoring Using Circumferential Changes of a Body Portion," filed Nov. 22, 2016, which claims priority to U.S. Provisional Patent Ser. No. 62/281,600, entitled "Wired and Wireless Plethysmographs Two-Way Linked to Mobile Application Software for Exercise, Health and Disease Monitoring," filed Jan. 21, 2016, each of which is herein incorporated by reference in its entirety.

TECHNICAL FIELD

This disclosure relates to the fields of health and wellness, and more specifically, to devices, systems, and methods for digitally monitoring one or more health, indicators of an individual, including circumferential changes to one or more body portions.

BACKGROUND

For many health conditions, an increased circumference of a patient's limb, torso, waistline, or other body portion is indicative of a negative health event. For example, a rapid increase in the circumference of a patient's leg is often due to edema—a swelling of the leg. Edema may be indicative of deep vein thrombosis, congestive heart failure, liver disease, kidney disease, an allergic reaction, inflammation caused by injury or infection, or other serious medical condition. Gradual increases in the circumference of a waistline or other body portion may be due to weight gain, which itself may be indicative of inactivity, overeating, depression, a hormonal imbalance, or other medically-relevant condition. On the other hand, for some individuals, such as those being treated for cancer, pregnant women, undernourished individuals, and athletes, a gradual increase in the circumference of a body portion may be desirable, and may be indicative of healthy weight gain, a growing fetus, or an increase in muscle mass. In each of the above scenarios, monitoring the circumference of a body portion may provide valuable insights into the health or wellness of an individual.

Early detection of circumferential changes of the body is crucial for some conditions such as deep vein thrombosis (DVT). DVT is characterized by the formation of a blood clot in a deep vein of a patient, typically in a patient's leg. Venous insufficiency and subsequent formation of a blood clot may cause considerable swelling, pain, redness, and increased body temperature near the clot. Additionally, patients with DVT are at risk of developing a pulmonary embolism (PE). PE can be a life-threatening complication, which occurs when a blood clot in a deep vein breaks loose, travels to the lungs, and blocks an artery in the lungs. It is estimated that 10-30% of patients die from DVT/PE within a month of diagnosis. In the United States of America, DVT/PE is estimated to cause 60,000-100,000 deaths each year. However, if the blood clot is identified early, when it is still developing in a deep vein, DVT can often be treated effectively with pharmaceutical agents designed to prevent the clot from growing or detaching and traveling to the lungs. If identified early, patients can also reduce the likelihood of clot growth and detachment through exercise. Accordingly, there is a critical need for early detection of DVT. Currently, detection means are lacking outside the clinical setting.

Certain risk factors greatly increase an individual's likelihood of developing DVT. For example, there is an increased prevalence of DVT in individuals whose limbs are immobile or inactive for long periods of time due to recovery after orthopedic surgery or other surgery, hospitalization, bed rest, or long-distance travel by airplane or automobile. Pregnancy, leg injuries, some prescription drugs, and some cancers are also known to increase a person's risk of developing DVT. The risk may be lowered through actions such as exercising, elevating the legs, abstaining from smoking, surgery, and taking a blood thinner or other pharmaceutical agent. Due to the importance of prevention and early detection of DVT, there is a need to monitor at risk individuals and encourage them to engage in activities and habits that lower their risk of developing pre-DVT conditions such as edema or DVT itself.

SUMMARY

As discussed above, there is a need for improved means for preventing and detecting DVT. In particular, there is a need for devices, systems, and methods that can encourage individuals to engage in activities and habits that lower their risk of developing DVT and associated pre-DVT conditions and that can determine whether an individual has complied with, prescribed recommendations. There is a need for devices, systems, and methods that can monitor an individual's limb to detect abnormal swelling and other symptoms associated with DVT. There is also a need, more generally, for devices, systems, and methods that can: detect swelling or other changes in the circumference of a body portion, provide relevant health or fitness recommendations to an individual and determine whether an individual has complied with, the recommendations. The present disclosure is directed to devices, systems, algorithms, and methods that fill one or more of these needs.

One aspect of the disclosure is directed to a method for monitoring health parameters of an individual, including circumferential changes to a portion of a body. The method includes obtaining a plurality of circumference measurements of the body portion, over a period of time via a sensor system, transmitting the circumference measurements from the sensor system to a mobile computing device, processing the circumference measurements to track and analyze any change in circumference of the body portion, and generating an alert output based, at least in part, on the analyzed change in circumference. In some embodiments, processing the circumference measurements to track and analyze any change in circumference is performed fully or partially by the mobile computing device. In some embodiments, processing the circumference measurements to track and analyze any change in circumference is performed fully or partially by a network computing device that may receive the circumference measurements from the mobile computing device. In some embodiments, the method further includes querying the individual for user inputs. In such embodiments, the alert output may also be based, in part, on these user inputs. Additionally or alternatively, in some embodiments, the method also includes transmitting the circumference measurements, user inputs, and/or other data acquired by the mobile computing device to a healthcare provider, coach, or other authorized user.

Another aspect of the disclosure is directed to a monitoring system configured to detect circumferential changes to a portion of a body. The monitoring system includes a sensor system wearable around a portion of an individual's body, which is configured to obtain and transmit a plurality of circumference measurements of the body portion over a period of time. The monitoring system also includes a mobile computing device, which includes a processor and a non-transitory computer-readable medium with instructions stored thereon. The instructions, when executed by the processor, cause the processor to: receive the transmitted circumference measurements, process the circumference measurements to track and analyze any change in circumference of the body portion, and generate an alert output based, at least in part, on the analyzed change in circumference. In some embodiments, the instructions stored on the computer-readable medium further cause the processor to query the individual for user inputs. In such embodiments, the alert output may also be based, in part, on these user inputs.

In some embodiments, the monitoring system is configured to monitor for abnormal swelling of a limb, for example, swelling caused by interstitial edema, deep vein thrombosis, pulmonary embolism, lymphedema, or other medical condition, in such embodiments, the monitored body portion may be, for example, one or both legs. The body portion of some embodiments includes the right and left legs of an individual, and the sensor system includes a first component configured to obtain a first plurality of circumference measurements over time from a fixed location on the right leg, and a second component configured to obtain a second plurality of circumference measurements over time from an equivalent fixed location on the left leg. In some such embodiments, processing the circumference measurements to track and analyze any change in circumference includes: comparing the first plurality of circumference measurements to each other to detect a change in the circumference of the right leg over time, comparing the second plurality of circumference measurements to each other to detect a change in the circumference of the left leg over time, and calculating a difference between the change in circumference of the right leg and the change in circumference of the left leg. The difference between the change in circumference of the right leg and the change in circumference of the left leg may contribute to a determination of a timing or content of the alert output. For example, the alert output may be generated when the difference between the change in circumference of the right leg and the change in circumference of the left leg exceeds a threshold value.

In some embodiments of the monitoring system, the user inputs prompted and received by the mobile computing device include symptoms and/or risk factor data. Additionally or alternatively, the user inputs may include an indication of whether the individual has complied with a pre-scribed instruction. The prescribed instruction may be prescribed by a healthcare provider or the monitoring system. In some embodiments, the prescribed instructions are customizable by a healthcare provider via a remote computing device communicatively coupled to the mobile computing device.

The mobile computing device may be farther configured to compute a compliance score indicative of the degree to which the individual complied with the prescribed instructions. The compliance score may be calculated based on one or more of: the change in circumference of the body portion, the user in puts, detected motion of the body portion indicative of an exercise, and a detected orientation of the body portion. For example, if the prescribed instructions include an instruction to upwardly tilt or elevate the legs, the compliance score may be determined, at least in part, by monitoring leg orientation. Such a sensor system may include a gyroscope, if the prescribed instructions include an instruction to perform leg exercises, the compliance score may be determined, at least in part, by monitoring leg movement. Such a sensor system may include an accelerometer. If the prescribed instructions include an instruction to administer a medication, the compliance score may be determined, at least in part, from a user-entered input indicating medication administration. Hie compliance score may be transmitted by the mobile computing device to a network computing device in order to be accessible to a healthcare provider or other authorized user.

In some embodiments of the monitoring system, the alert output includes an instruction to the individual to consult a healthcare provider for evaluation. In some embodiments, the alert output is generated when an overall score exceeds a predefined threshold. The overall score may correspond to a likelihood of onset of a disease that causes abnormal swelling of a limb. For example, the overall score may correspond to the likelihood that the individual has developed interstitial edema, deep vein thrombosis, pulmonary embolism, or lymphedema. Various parameters may contribute to the overall score, including one or more of: the change in circumference of the body portion, a skin temperature at the body portion, a skin color at the body portion, one or more user inputs related to symptoms or risk factors, and the compliance score.

In some embodiments, the monitoring system is configured to monitor for changes in the circumference of a body portion resulting from weight gain, weight loss, the development of a fetus within a woman's uterus, or changes in muscle mass. In such embodiments, the body portion, may include one or more of a limb (or limbs), an upper torso (i.e., chest), and a lower torso (i.e., waist). The user inputs prompted and received by the mobile computing device may include data inputs related to one or more of: an exercise performed, a food consumed, a supplement consumed, a medication administered, duration of sleep, and a user-perceived wellness rating. The alert output may include an evaluation of weight loss progress, fetal development, or strength training effectiveness or progress. The mobile computing device of the monitoring system may be further configured to output guidance, such as recommended exercises, meal plans, and/or other wellness tips and reminders tailored to the individual based on one or more of: the change in circumference of the body portion, detected movement of the body portion, and the user inputs.

In various embodiments of the monitoring system, the sensor system includes a stretchable component and a sensor module coupled thereto. The stretchable component is configured to fit securely around the body portion. The stretchable component may be formed of a stretchable band, sleeve, belt, brace, or garment such as a sock, legging, or shirt. In some embodiments, the sensor module comprises: an electrical component configured to undergo a change when the stretchable component is stretched, and a sensor configured to detect the change. The change may include a change in a parameter such as inductance, resistance, or capacitance. In such embodiments, the changed parameter correlates to, and is indicative of, a change in circumference. In some embodiments, the sensor module includes a strain gauge configured to detect a tensile force exerted on the stretchable component, the force being correlated to, and indicative of a circumference measurement.

In some embodiments, the sensor system is further configured to detect one or more of: a surface skin temperature, an orientation of the body portion, an acceleration of the body portion, and a color of a surface of the body portion. Such a sensor system may include one or more of: a temperature sensor, a gyroscope, an accelerometer, and an image sensor.

In some embodiments, the monitoring system also includes a network computing device communicatively coupled to the mobile computing device and configured to receive and store the circumference measurements and other data received from the mobile computing device, generate and transmit alerts to a healthcare provider or other authorized user, and store and transmit instructions and information to the mobile computing device. In some embodiments, the monitoring system also includes a supervisor computing device communicatively coupled to the network composing device. In some such embodiments, at least some of the instructions and information transmitted from the network computing device to the mobile computing device are customizable by a healthcare provider, coach, or other health or wellness professional via the supervisor computing device.

An additional aspect of the disclosure is directed to a leg monitoring device. The leg monitoring device of various embodiments includes: a stretchable component configured to fit securely around a circumference of a patient's calf, and a sensor module coupled to the stretchable component. The sensor module includes various electrical components, for example, a battery, a first sensor configured to sense a first parameter indicative of the circumference of the patient's calf, a processing unit configured to process the first parameter and detect a circumference measurement from the first parameter, a memory storage configured to store the circumference measurement, and an antenna configured to wirelessly transmit the circumference measurement to a paired mobile computing device.

In some embodiments, the first parameter is selected from a group consisting of: inductance, resistance, capacitance, and strain. In some embodiments, the stretchable component includes a stretchable band, sleeve, belt, brace, or garment In some embodiments, at least a portion of the sensor module is reversibly coupled to the stretchable component. In some embodiments, the leg monitoring device is configured to detect swelling of the patient's calf consistent with the onset of interstitial edema, deep vein thrombosis, pulmonary embolism, or lymphedema. In some embodiments, the sensor module also includes a second sensor configured to sense a second parameter indicative of motion of the patient's calf. The second sensor may be an accelerometer. Additionally or alternatively, the sensor module may include an additional sensor configured to sense an additional parameter indicative of an orientation of the patient's calf. The additional sensor may be a gyroscope. In some embodiments, the sensor module additionally or alternatively includes one or more of a temperature sensor and an image sensor. In some embodiments, the sensor module is configured to provide a measurement of tightness of the stretchable component. In some embodiments, the leg monitoring device or a mobile computing device communicatively coupled thereto is configured to generate an alert when the sensor module detects that the stretchable component is too tight. In some embodiments, the leg monitoring device generates a haptic alert. In some embodiments, a mobile computing device communicatively coupled to the leg monitoring device is configured to generate outputs that include health-related feedback and/or recommendations based on one or more of the sensor readings.

BRIEF DESCRIPTION OF THE DRAWINGS

The foregoing is a summary, and thus, necessarily limited in detail. The above-mentioned aspects, as well as other aspects, features, and advantages of the present technology will now be described in connection with various embodiments, with reference made to the following accompanying drawings;

FIGS. 7A-7F schematically illustrate a plurality of examples of graphical user interfaces displayed by the mobile, computing device of FIG. 6.

Figure 1:
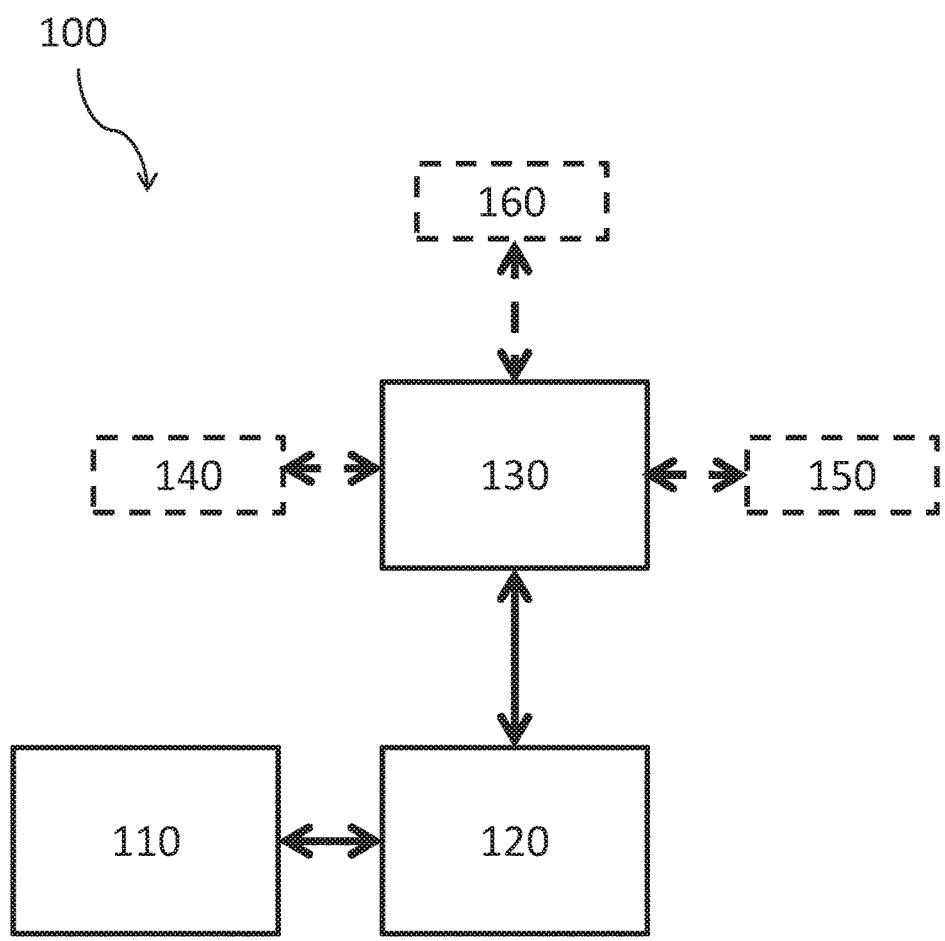
FIG. 1 illustrates a schematic block diagram of one embodiment of a system for monitoring health parameters of an individual, including circumferential changes to a portion of a body.

The illustrated embodiments are merely examples and are not intended to limit the invention.

DETAILED DESCRIPTION

The following description is not intended to limit the invention to these described embodiments, but rather to enable any person skilled in the art to make and use this invention. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure.

Throughout and within this specification, one or more publications may be referenced to more fully describe the state of the art. The disclosures of each of these references are incorporated herein by reference in their entireties as though they also form part of this disclosure.

Unless otherwise defined, each technical, or scientific term used herein has the same meaning as commonly understood by one of ordinary skill in the art to which this disclosure belongs.

As used in the description and claims, the singular form "a", "an" and "the" include both singular and plural references unless the context clearly dictates otherwise. For example, the term "a limb" may include, and is contemplated to include, a plurality of limbs. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., a change in force or circumference), indicates approximations which may vary, for example, by (+) or (−) 5%. All numerical ranges provided herein are inclusive of the stated start and end numbers. The term "substantially" indicates mostly (i.e., greater than 50%) or essentially all of an element, process, component, device, or system.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention "Consisting of" shall mean that the devices, systems, and methods include the recited elements and exclude anything more than a trivial or inconsequential element or step. Embodiments defined by each of these transitional terms are within the scope of this disclosure.

Overview

Disclosed herein are devices, systems, and methods for monitoring one or more health parameters of an individual, including circumferential change to one or more body portions. The devices, systems, and methods of various embodiments are additionally intended to track and increase compliance with health and wellness recommendations and improve health and wellness outcomes.

FIG. 1 illustrates one example of a health monitoring system configured to obtain, analyze, and respond to circumference measurements of a body portion of an individual. As illustrated, the monitoring system 100 includes a sensor system 110, a mobile computing device 120, and a network computing device 130. The system 100 may additionally be configured to form a connected network in which physicians, coaches, and/or other authorized users can track the progress of the monitored individual and/or individualize instructions and feedback provided to the monitored individual. In such embodiments, the health monitoring system 100 includes one or more additional computing devices, including one or more supervisor computing devices 140, one or more reviewer computing devices 150, and/or one or more administrator computing devices 160.

In various embodiments, the sensor system 110 is configured to be worn by a subject. A subject who wears the sensor systems described herein may be interchangeably referred to as a user, patient, individual person, or athlete. It will be appreciated by those skilled in the art that the subject monitored by the various devices and systems described herein may be any mammal or other animal.

The sensor system 110 is formed of: a stretchable component configured to fit securely around a body portion of the individual, and a sensor module coupled thereto. The stretchable component may be a strap, brace, belt, garment, or other wearable material designed to be fitted around the body portion. As used herein, the body portion may refer to one or both legs, one or both arms, a torso, a chest, a belly, a waist, a head, and/or other body part. The sensor module is configured to sense the amount of stretch experienced by the stretchable component and detect a circumference measurement from the sensed stretch. As used herein, the sensor module includes all sensors, power supply, signal processing electronics, controlling logic, and digital transmission devices needed to sense the stretch, obtain circumference measurements of the body portion, and transmit the circumference measurements to the mobile computing device 120. The sensor module may additionally include other sensors such as sensors configured to detect orientation, acceleration, temperature, and/of color.

As used herein, the mobile computing device 120 refers to both the hardware and the application software of the computing device that communicates with the sensor system 110. The mobile computing device 120 is configured to receive, process, and analyze sensor data from the sensor system 110. It may be further configured to query an individual for user inputs, generate reminders and other alerts to the individual, provide access to relevant health-related information, and generate and transmit messages intended for physicians, coaches, caregivers, or other authorized users of the system.

In some embodiments, the mobile computing device 120 is a smartphone, wearable computing device, notebook computer, laptop computer, tablet, or other portable computing device configured to pair with the sensor system 110. In other embodiments, the mobile computing device 120 may be any other personal computing device configured for wired or wireless connection to the sensor system 110.

As shown in FIG. 1, the mobile computing device 120 is connected, at least at times, to the sensor system 110 via a communication link. In some embodiments, the mobile computing device 120 is wirelessly coupled to the sensor system 110 via a nearfield communications (NFC) protocol, a low energy Bluetooth® protocol, or other radiofrequency (RF) communication protocol. In some embodiments, the sensor system 110 is additionally or alternatively configured to communicate with the mobile computing device 120 via a databus and a wired (e.g., removable cable) connection. In some embodiments, communication between the sensor system 110 and the mobile computing device 120 is bidirectional; in other embodiments, communication is unidirectional with data pushed from the sensor system 110 to the mobile computing device 120.

In various embodiments, the mobile computing device 120 is coupled to the network computing device 130 via a bidirectional communication link. In particular, the mobile computing device 120 may be connected to the network computing device 130 via a CDMA, GSM, LTE, or other cellular network, via Wi-Fi®, or via any other suitable wireless or wired communication protocol. If one or more supervisor computing devices 140, reviewer computing devices 150, and/or administrator computing devices 160 are present in the system, such devices are also connected to the network computing device 130 via a bidirectional communication link, such as a cellular network, Wi-Fi, other wireless communication protocol, or via a cable internet, dial-up internet, Ethernet or other wired means of connection.

The network computing device 130 of some embodiments is a cloud-based server. It may be formed of one or multiple computing devices, including an application server, an internet server, a database server, or a combination thereof. In some embodiments, the network computing device 130 is operated, managed, controlled, maintained, or owned by a system administrator. The network computing device 130 refers to the hardware and software that contains and implements an analytics system. The analytics system refers to the backend system that stores all user data. It also stores all instructions that are transmitted to and downloadable by the mobile computing device 120. These include application instructions (i.e., software) and prescribed health-related instructions intended for the monitored individual. The analytics system of some embodiments is also configured to perform analytics of a monitored individual's data and population-wide data. The analytics system may also be configured, for integration with electronic medical records.

In some embodiments, one or more supervisor computing devices 140 are provided within the monitoring system. As used herein, a supervisor computing device 140 is any computing device used by a health or wellness professional to interact with the analytics system of the network computing device 130. As used herein, a health or wellness professional is also referred to as a supervisor and is intended to include any individual who oversees an aspect of the care, health, or wellness of the monitored individual. The supervisor may be, for example, an athletic coach, personal trainer, or healthcare provider. A healthcare provider, as used herein, refers to a professional responsible for the healthcare of the monitored individual. The healthcare provider may be a physician, physician assistant, medical technologist, other medical assistant, nurse, nurse practitioner, podiatrist, chiropractor, dietician, midwife, or any other healthcare professional In some embodiments, a supervisor is able to access an application-based or web-based internet portal using the supervisor computing device 140, which enables the supervisor to interact with the analytics system of the network computing device 130. Through the supervisor portal, the supervisor can: review data acquired from the sensor system 110; configure and modify alert algorithms, which the monitoring system uses to determine when to generate alerts for the monitored individual and what alerts to generate; create, customize, and/or modify prescribed instructions for the monitored individual; select specific parameters for the sensor system 110 to monitor; and select or compose messages for transmission to the mobile computing device 120 of the monitored individual.

Additionally or alternatively, in some embodiments, one or more reviewer computing devices 150 are provided within the monitoring system. As used herein, a reviewer computing device 150 is any computing device used by a reviewer to interact with the analytics system of the network computing device 130. As used herein, a reviewer is any trusted individual who has been granted access, by a monitored individual or a supervisor, to review the data of a particular monitored individual. The reviewer may be a caregiver, friend, family member, guardian, or other individual concerned, with the welfare of the monitored individual. In some embodiments, a reviewer is able to access an application-based or web-based internet portal using the reviewer computing device 150, which enables the reviewer to interact with the analytics system of the network computing device 130. Through the reviewer portal, the reviewer may be able to: review all or a limited portion of the data acquired from the sensor system 110; select or compose messages of encouragement or other feedback for transmission, to the mobile computing device 120 of the monitored individual; and/or generate and send questions to a healthcare provider or other supervisor.

The network computing device 130 may include one or more input devices, output devices, and/or communicatively coupled administrator computing devices 160 through which a system administrator can create and maintain the analytics system.

Each of the supervisor computing devices 140, reviewer computing de vices 150, and administrator computing devices 160 may be any suitable computing device, including, for example, a smartphone, wearable computing device, notebook computer, laptop computer, tablet, or desktop computer.

Together, the components of the monitoring system 100 function to execute various algorithms and perform various methods, including obtaining, analyzing, and responding to circumference measurements of a body portion.

Figure 2:
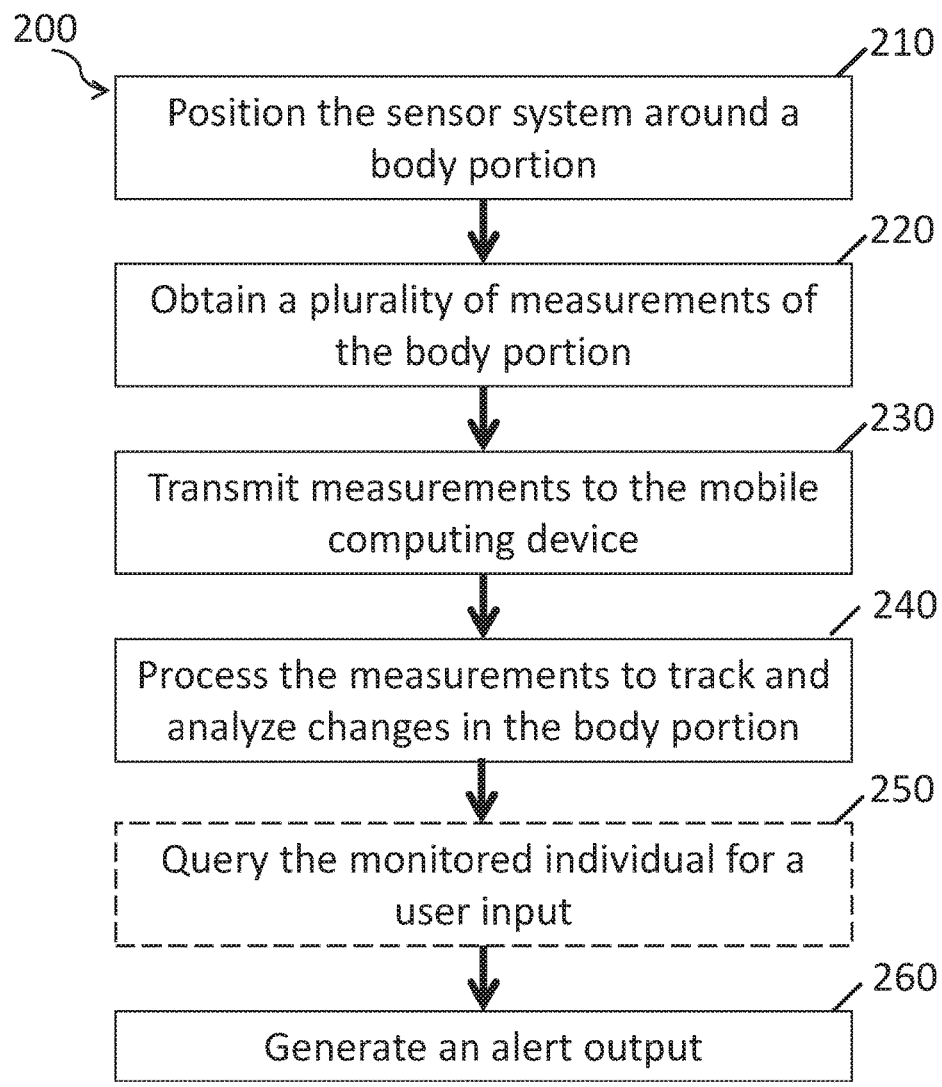
FIG. 2 illustrates a flow chart of one embodiment of a method of using the monitoring system of FIG. 1.

FIG. 2 depicts one example of a method 200 of using the monitoring system 100 described above. As shown at block 210, the method includes positioning the sensor system 110 around a body portion. The sensor system 110 may be secured around the body portion by the monitored individual or with the help of a physician, athletic trainer, other supervisor, friend, family, caregiver, or other reviewer. The sensor system 110 of some embodiments is reusable and configured to permit repeated attachment to and detachment from the body portion. In some embodiments, the sensor system 110 is shaped to conform, to one or more contours of the individual's body or is otherwise configured so as to facilitate accurate positioning of the sensor system 110 at the same location each time it is worn.

As shown at block 220, the method 200 further includes obtaining a plurality of measurements of the body portion via the sensor system 110, including, for example, a plurality of circumference measurements. As described in more detail in the next section, in some embodiments, obtaining the plurality of measurements includes: obtaining a baseline, sensing a change in a parameter indicative of and correlated to a change in circumference, and calculating a circumference measurement from the sensed change in the parameter. The calculated circumference measurement may be a relative measurement (i.e., a measure of change from the baseline or from a previous measurement). In some embodiments, obtaining a plurality of measurements of the body portion further includes obtaining measurements (e.g., absolute or relative measurements) of one or more additional health-related parameters. For example, in some embodiments, the sensor system 110 is configured to obtain measurements indicative of one or more of a change in: orientation, movement (i.e., acceleration), color, and temperature of the body portion. Additionally or alternatively, in some embodiments, the sensor system 110 is configured to obtain measurements indicative of pulse, heart rate, blood oxygenation (i.e., pulse oximetry), blood volume (i.e., plethysmography), and/or other health parameters.

The method 200 also involves transmitting the measurements from the sensor system 110 to a communicatively coupled mobile computing device 120, as shown at block 230. The transmitted measurements may include any obtained by the sensor system 110, including, for example, circumference, orientation, acceleration, color, and/or temperature.

At block 240, the measurements are processed to track and analyze changes in the body portion. In some embodiments, circumference measurements are tracked over time and changes are analyzed, for example, to determine when the circumference change has exceeded a predefined threshold value. Similarly, any other parameters being measured may be tracked over time and analyzed. In some embodiments, each measured parameter contributes to an overall risk score or wellness score, and analyzing the measurements involves weighting the changes in each parameter, calculating an overall score, and determining if the score has exceeded a predefined threshold value. In some embodiments, processing the measurements to track and analyze changes is performed partially or fully by the mobile computing device 120. Additionally or alternatively, in some embodiments, some of or all the processing, tracking, and analysis is performed on the sensor system 110. Additionally or alternatively, in some embodiments, some of or all the processing, tracking, and analysis is performed by a network computing device 130.

Optionally, in some embodiments, the method 200 further includes querying the individual for user inputs, as shown at block 250. Such queries are presented to a monitored individual on the mobile computing device 120. The requested user inputs may vary depending on the intended use of the monitoring system 100. For example, the mobile computing device 120 may prompt a user to enter one or more of: biographical information, the user's current weight, medical history, current symptoms, risk factor data, a pregnancy status (e.g., a gestation age, conception date, or due date), an exercise performed, a food consumed, a supplement consumed, a medication administered, a duration of sleep attained, a daily wellness rating, and an indication of whether the monitored individual has complied with a prescribed instruction.

The monitoring system 100 generates an alert output at block 260. The alert output may be a visual, tactile, and/or audio output generated by the mobile computing device 120. The alert output may provide a warning, recommendation, positive feedback, progress alert, or any other useful message. The alert output is based, at least in part, on the analyzed change in circumference. For example, the alert output may be generated by the mobile computing device 120 upon detecting that the circumference change exceeded a predefined threshold. In other embodiments, the alert output is generated by the mobile computing device 120 at a regular time interval, and the information conveyed in the alert output varies depending on the body portion's change in circumference. In some embodiments, the alert output may also be based, in part, on the analysis of other parameters being measured and/or the user inputs. In some embodiments, alert outputs may also be transmitted to one or more supervisor and/or reviewer computing devices to alert a supervisor or reviewer of important changes, progress, or status of the monitored individual.

Sensor System

Figure 3:
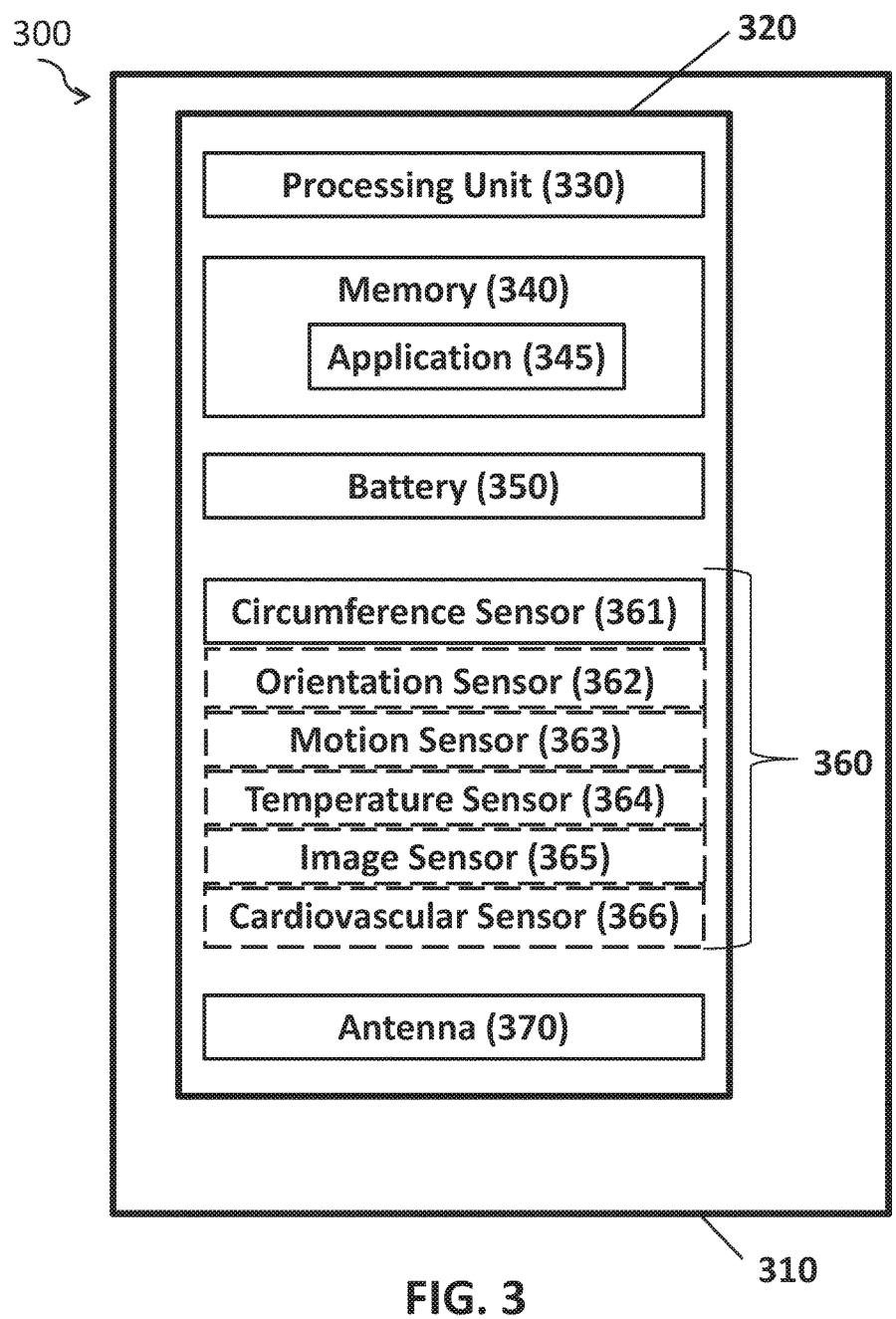
FIG. 3 illustrates a functional block diagram of one embodiment of a sensor system provided within the monitoring system of FIG. 1.

A functional block diagram of one embodiment of a sensor system is provided in FIG. 3. While numbered uniquely, one skilled in the art will appreciate that the sensor system 110 of FIG. 1 may be formed of any embodiment of a sensor system described herein and may include any of or all the functional components described with respect to the sensor system 300 shown in FIG. 3. Moreover, although illustrated separately, it is to be appreciated that the various functional blocks of the sensor system 300 need not be separate structural elements.

The sensor system 300 of various embodiments includes a stretchable component 310 configured to fit securely around the body portion, and a sensor module 320 coupled thereto. In some embodiments, at least a portion of the sensor module 320 is removable from the stretchable component 310. For example, the stretchable component 310 may be formed of a machine-washable fabric, and at least a portion of the sensor module 320 may be housed within a protective casing that is detachable from the stretchable component 310. In some embodiments, a first portion of the sensor module 320 is integrated into the stretchable component 310 while a second portion is positioned within the protective casing. For example, a processing unit 330 and a battery 350 may be stored within the casing, while a strain gauge, resistor, and/or other sensing components 360 of the sensor module 320 may be weaved into, disposed within, printed on, affixed to, or otherwise integrated into the fabric of the stretchable component 310.

As shown in FIG. 3, the sensor module 320 includes a processing unit 330, which may be a general purpose microprocessor, a digital signal processor (DSP), a field programmable gate array (FPGA), an application specific integrated circuit (ASIC), or other programmable logic device, or other discrete computer-executable components designed to perform the algorithms and functions described herein. The processing unit 330 may also be formed of a combination of computing devices, for example, a DSP and a microprocessor, a plurality of microprocessors, one or more microprocessors in conjunction with a DSP core, or any other suitable configuration.

In various embodiments, the processing unit 330 is coupled, via one or more buses, to the memory 340 in order for the processing unit 330 to read information, from and write information to the memory 340. The processing unit 330 may additionally or alternatively contain memory 340. The memory 340 can include, for example, processor cache. The memory 340 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include application software 345 stored in a non-transitory format. The software, when executed by the processing unit 330, causes the processing unit 330 to perform one or more operations described elsewhere herein.

In various embodiments, a power supply, such as a battery 350, is electrically coupled to provide power to the processing unit 330 and other electronic components. The battery 350 may be rechargeable or disposable. Additionally, some embodiments of the sensor module 320 may include one or more signal processing components, such as a filter (e.g., low-pass, high pass, or band pass filter), an amplifier, and/or an analog-to-digital (AD) converter.

As shown, the sensor module 320 includes one or more sensors 360 configured to detect parameters indicative of the monitored individual's health. For example, the sensor module 320 includes a circumference sensor 361 configured to detect changes in the circumference of the body portion. The circumference sensor 361 may detect a change in circumference indirectly. For example, when the body portion expands in circumference, the stretchable component 310 positioned around the body portion experiences an increase in tensile stress that causes strain (i.e., a physical deformation) in the stretchable component 310. In some embodiments, the circumference sensor 361 includes an electrical component positioned on or embedded within the stretchable component 310. The electrical component may itself experience strain in response to the increased tensile forces in the stretchable component 310. This increased strain in the electrical component changes the electrical conductance, and thus, the inductance, resistance, and/or capacitance of the component in a known, predictable manner. Thus, the strain can be calculated from a detected change in inductance, resistance, and/or capacitance of the electrical component. In turn, the processing unit 330 is configured to calculate a change in circumference from the detected change in inductance, resistance, and/or capacitance and obtain an absolute or relative circumference measurement. The electrical component, may be a foil strain gauge, semiconductor strain gauge (e.g., a piezoresistor), a nanoparticle-based strain gauge, a capacitive strain gauge, any other resistor, or any other suitable electrical component that experiences a detectable change in electrical properties in response to strain.

In some embodiments, the sensor module 320 additionally includes one or more of an orientation sensor 362, a motion sensor 353, a temperature sensor 364, an image sensor 365, and one or more cardiovascular sensors 366. The orientation sensor 362 of some embodiments is a gyroscope configured to detect when the body portion has tilted, been elevated, or otherwise changed position. The motion sensor 363 of some embodiments is an accelerometer configured to detect changes in motion such as repetitive changes in motion indicative of exercise. The temperature sensor 364 of some embodiments is a thermistor, thermometer, or other temperature-responsive sensor configured to detect changes in skin temperature at the body portion. The image sensor 365 of some embodiments is a camera, semiconductor charge-coupled device (CCD), or complementary metal-oxide-semiconductor (CMOS) configured to detect changes in the attenuation of light waves indicative of changes in skin color at the body portion. The one or more cardiovascular sensors 366 may include, for example, a pulse oximeter, a plethysmograph sensor, a pulse rate monitor, and/or a heart rate monitor.

In various embodiments, some of or all the measurements obtained by the sensor system 300 are transmitted wirelessly, for example, via a communication antenna 370, to the mobile computing device 120 for processing, analysis, and storage. The communication antenna 370 may be, for example, a transmitter or a transceiver. The measurements may be automatically pushed to the mobile computing device 120 or retrievable by a request, from the mobile computing device 120.

Various, non-limiting embodiments of the sensor system 300 are provided in FIGS. 4A-4K. As shown, each sensor system 300 includes a stretchable component 310 and a sensor module 320. While the sensor module 320 is largely positioned within a protective casing that houses many of the electrical components, at least a portion of the circumference sensor extends outside of the casing and is positioned to experience strain induced by the circumference of the body portion. In some embodiments, such as the embodiments of FIGS. 4A-4B, the sensor system 300 is formed of a strap, band, or belt. The entirety of the strap, band, or belt may be deformable and circumferentially stretchable, or only a portion of it may be configured to stretch. The strap, band, or belt may be sized and configured for placement on an upper torso or chest or lower torso or waist, as in FIG. 4A. Alternatively, it may be sized and configured for placement on a limb, such as an upper arm, lower arm, upper leg, or lower leg, as in FIG. 4B.

In various embodiments, the sensor system 300 is removable and configured for repeated reattachment. In order to achieve consistent, reliable, and accurate results, it is desirable for the various sensors to be located at the same locations with each reattachment. To facilitate proper positioning of the sensors, in some embodiments, the sensor system 300 is integrated into clothing or a brace. For example, one or more stretchable components 310 and sensor modules 320 may be integrated into a shirt (FIG. 4C), sports bra, shorts, leggings or pants (FIG. 4D), underwear, compression socks or other socks (FIG. 4E), partial socks or sleeves (FIG. 4F), knee brace (FIG. 4G), ankle brace (FIG. 4H), or any other suitable garment.

Figure 4A:
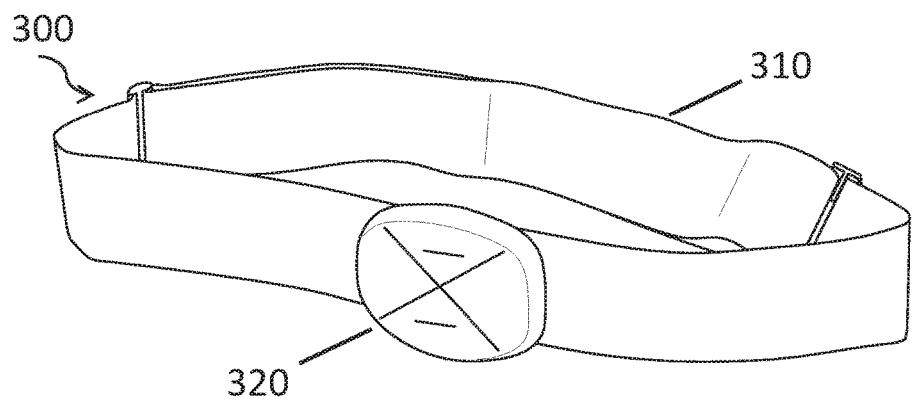
FIGS. 4A-4K schematically illustrate a plurality of examples of the sensor system of FIG. 3.
Figure 4B:
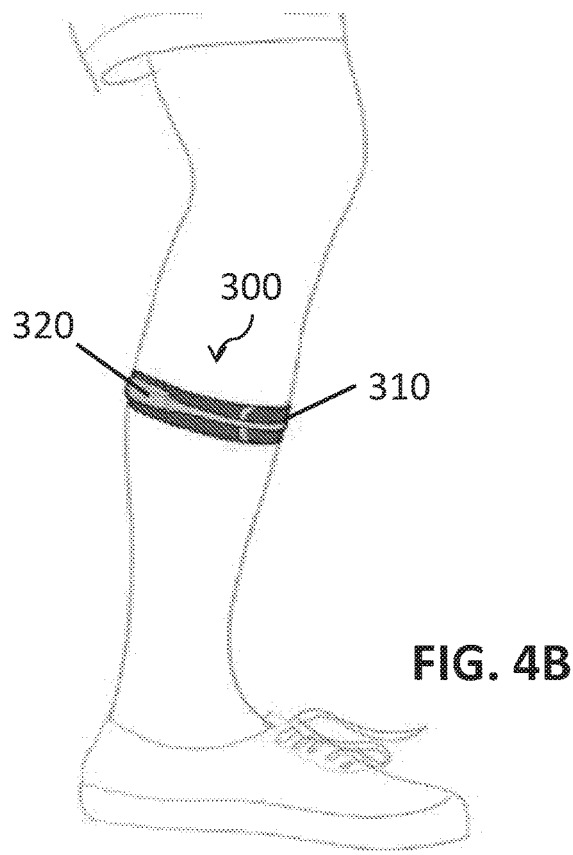
Figure 4C:
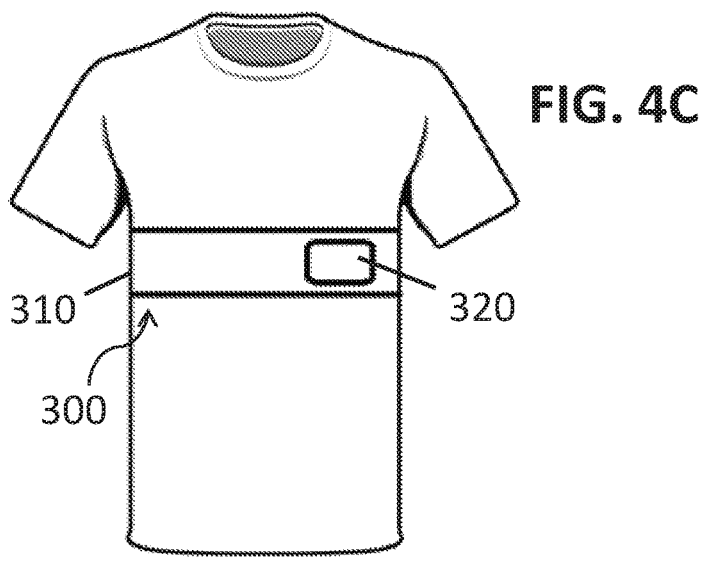
Figure 4D:
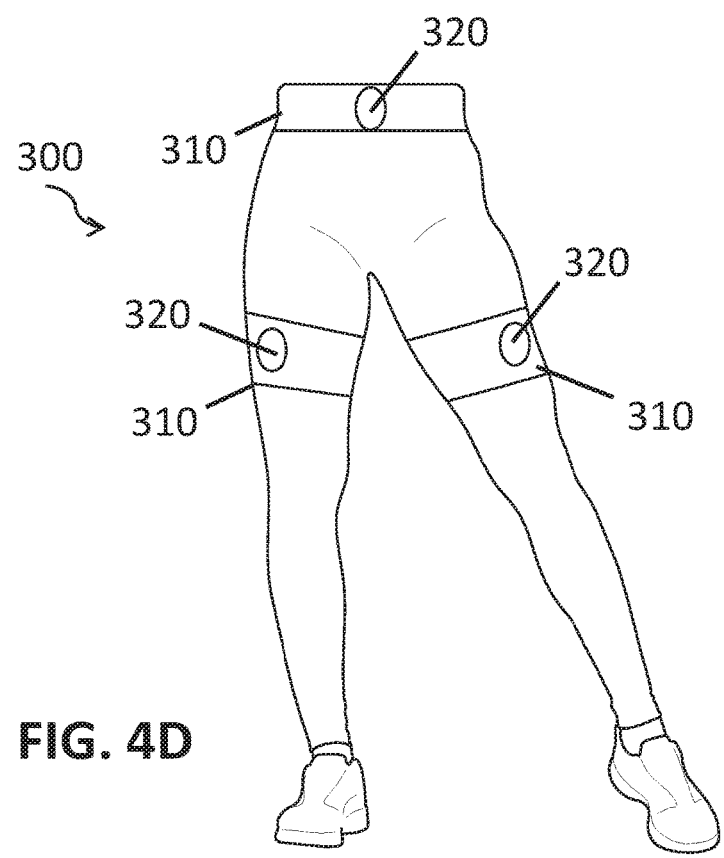
Figure 4E:
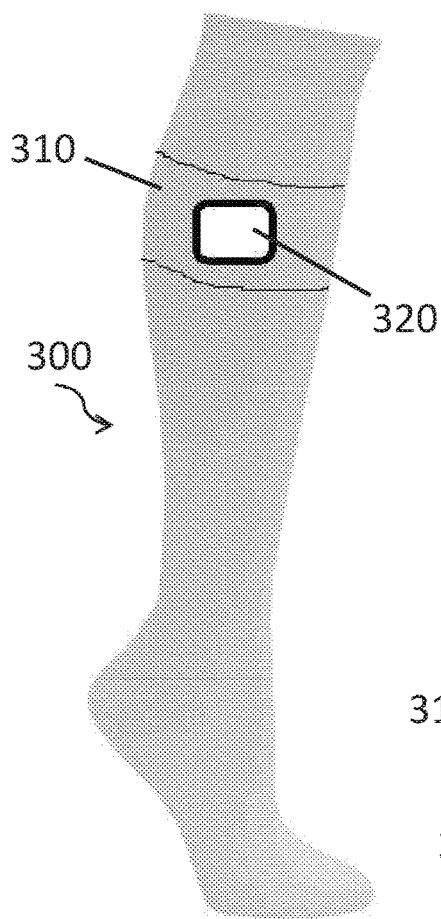
Figure 4F:
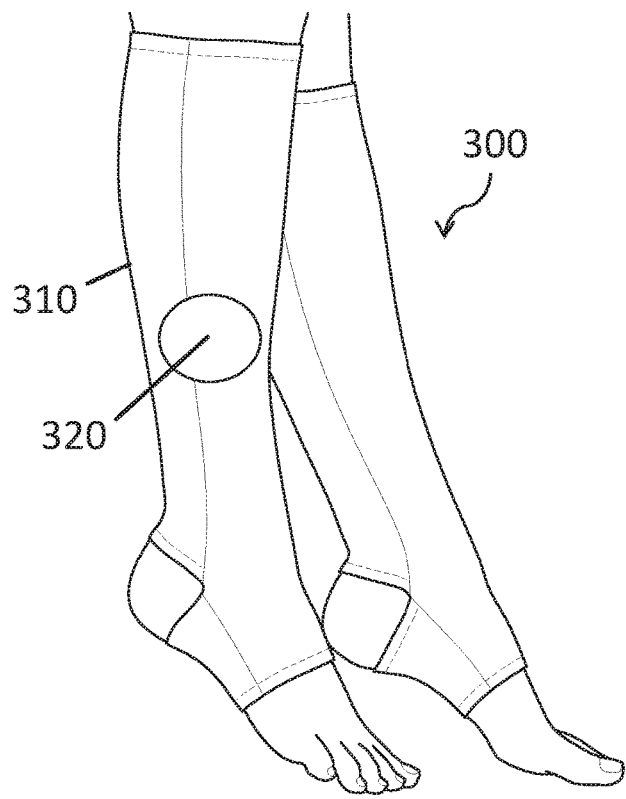
Figure 4G:
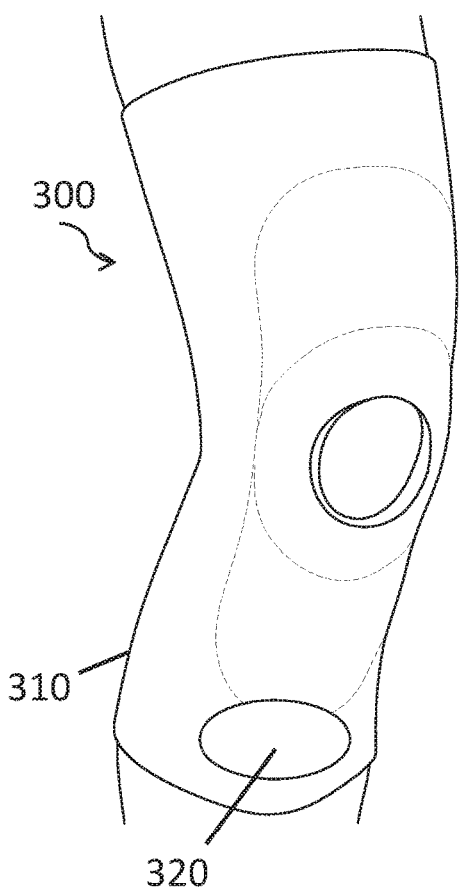
Figure 4H:
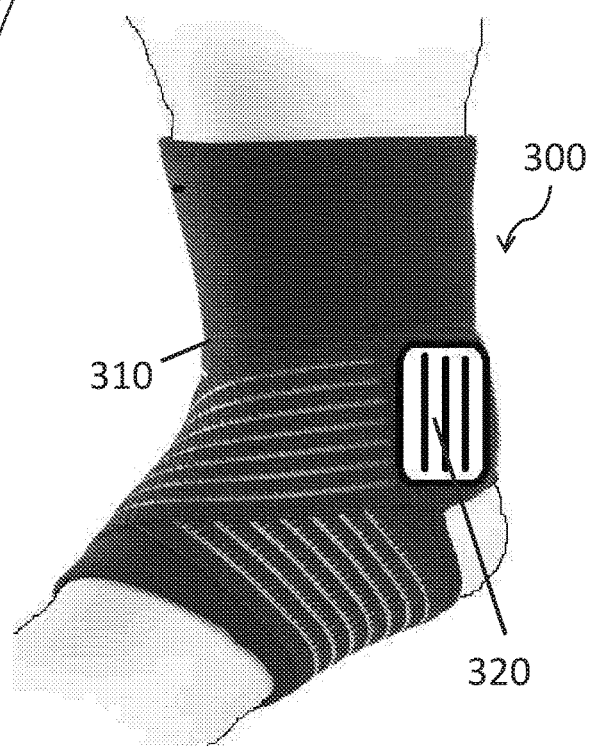
Figure 4I:
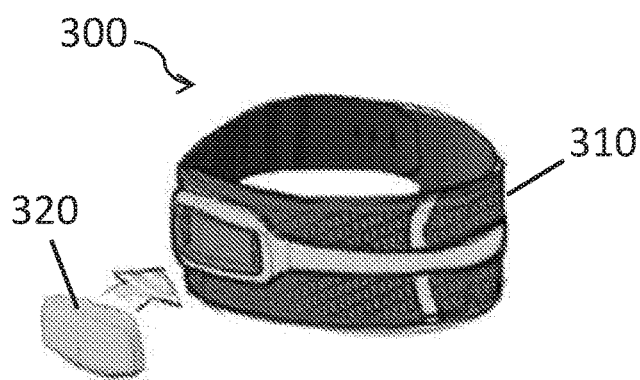
Figure 4J:
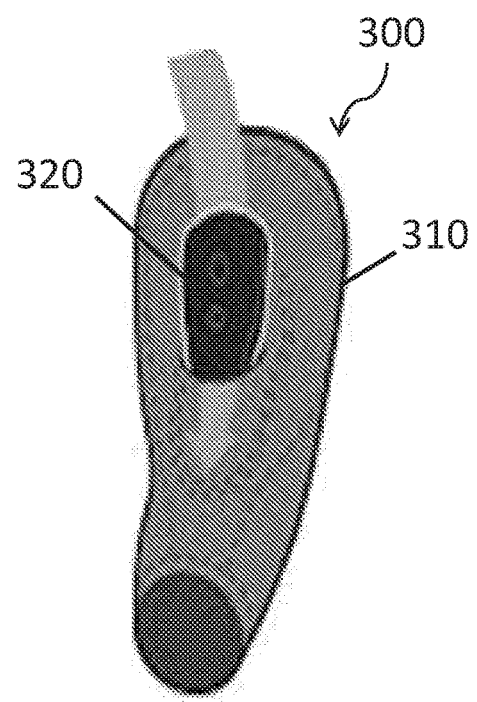

In some embodiments. Including any of the embodiments described with respect to FIGS. 4A-4K, at least a portion of the sensor module 320 is removable. This is illustrated, for example, with the band provided in FIG. 4I and the leg sleeve/tube provided in FIG. 4J. The removable portion of the sensor module 320 may be securable to the stretchable component 310 via any suitable attachment mechanism. For example, the stretchable component 310 may include a cradle or holder sized to receive the removable portion of the sensor module 320, and the removable portion of the sensor module 320 may snap or clip into the holder, as shown in FIG. 4I. Alternatively, the removable portion of the sensor module 320 may zip or hook into place, or it may slide between layers or into a pocket of the stretchable component 310, as shown in FIG. 4J. In some such embodiments, the stretchable component 310 is washable. In some embodiments, the removable portion of the sensor module 320 is enclosed in a water-resistant or water-proof protective casing. In some embodiments, the removable portion of the sensor module 320 may house the processing unit 330 and any associated electrical filtering and processing components, the battery 350, an accelerometer, a gyroscope, and/or one or more additional parameter sensors. In some embodiments, the removable portion is interchangeable and configured for attachment to a plurality of garments and devices. In some embodiments, the removable portion is automatically activated upon attachment to a garment or automatically deactivated upon detachment from a garment.

Figure 4K:
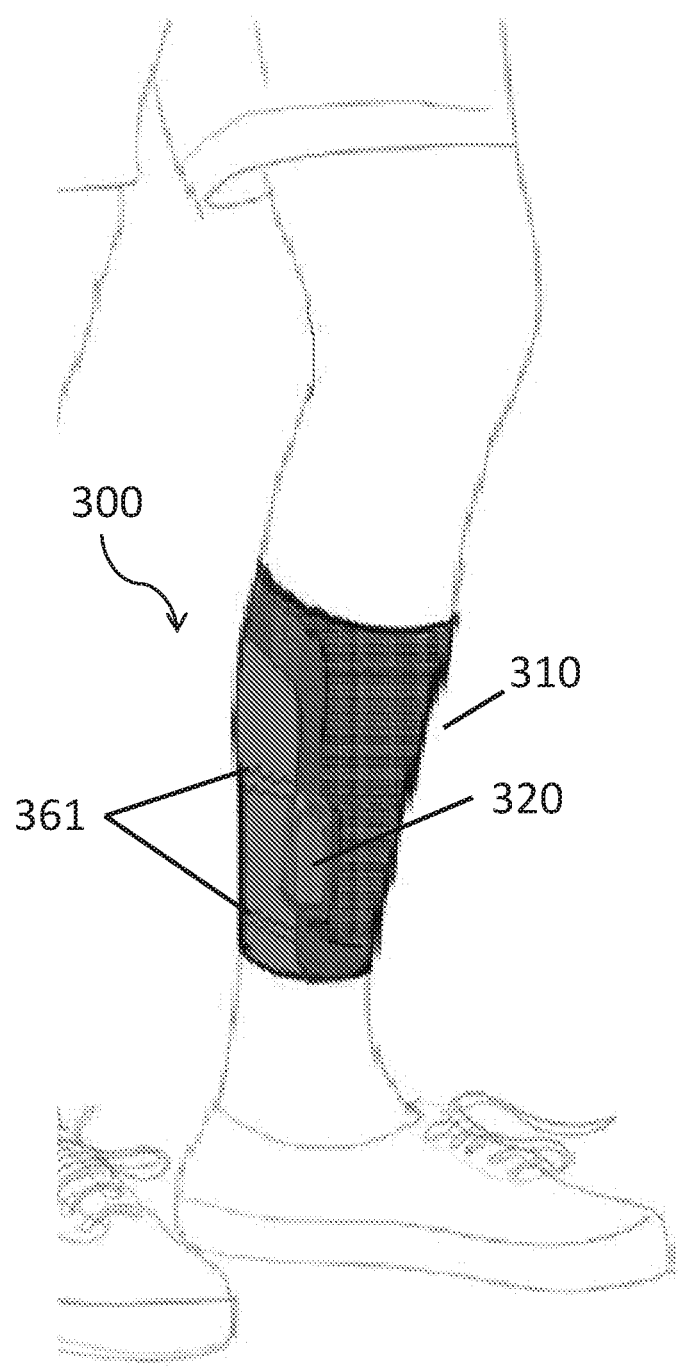

In FIG. 4K, the portion of the circumference sensor 361 that is integrated into the stretchable component 320 is schematically drawn, with visible lines to improve understanding. One skilled in the art will appreciate that each of the sensor systems 300 provided herein may have a similar feature, but in FIGS. 4A-4J, such a feature is not visible from the outside of the device. The depicted circumference sensor 361 may be any strain gauge or other suitable device described elsewhere herein. Additionally, as shown in FIG. 4K, any of the sensor systems 300 of FIGS. 4A-4K may include multiple circumference sensors 361 (e.g., two, three, or more sensors) in order to sense a parameter indicative of circumference at a plurality of locations of the body portion.

Figure 5:
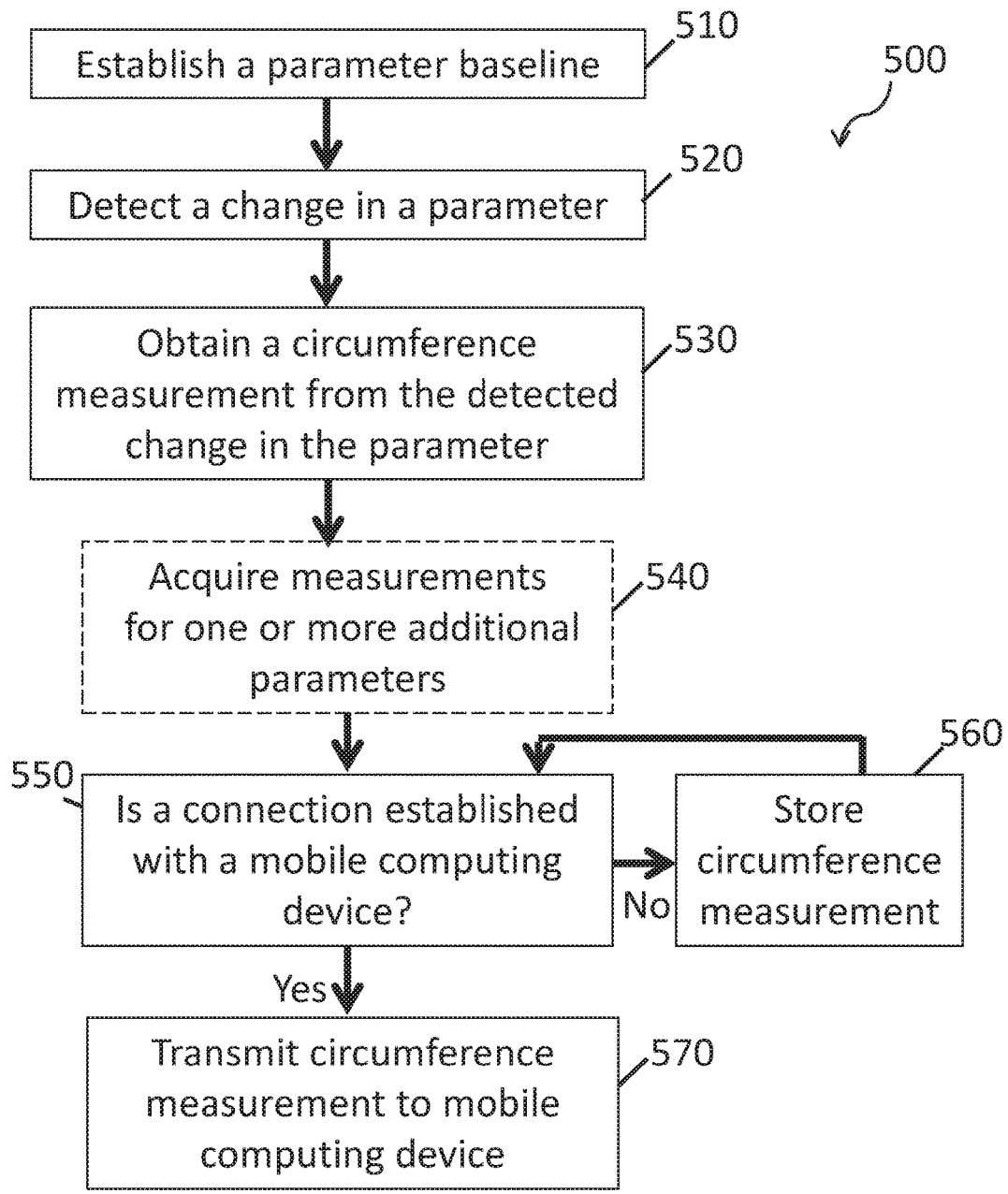
FIG. 5 illustrates a flow chart of one embodiment of a method performed by the sensor system of FIG. 3.

FIG. 5 depicts one example of a method 500 performed by the sensor system 300 described above. As shown at block 510, the method includes calibrating the sensor system 300 to establish a parameter baseline. When the sensor system 300 is first positioned on an individual, the stretchable component 310 will experience some degree of strain. As described above, strain may be detectable by a circumference sensor 361, which is formed of an electrical component positioned on or embedded within the stretchable component 310. The electrical component may itself be deformable in response to tensile stress and may experience a change in electrical properties when deformed, resulting in a change in a parameter such as the inductance, resistance, and/or capacitance of the electrical component. Following positioning of the sensor system 300 on the body portion, the initial parameter reading is set as the baseline. In some embodiments, the processing unit 330 calculates an actual baseline strain and/or circumference measurement, setting the baseline to that value, hi other embodiments, measurements are relative, and the initial parameter readings establish the zero value. As part of the calibration process, the sensor system 300 of some embodiments performs a status check. For example, in some embodiments, the processing unit 330 of the sensor module 320 checks to ensure each sensor is operational; in some embodiments, it determines whether the stretchable component 310 is experiencing a level of strain below a safety threshold, hi some embodiments, the sensor system 300 or a mobile computing device communicatively coupled thereto is configured to generate an alert if the sensor module 320 detects that the stretchable component 310 is too tight In some embodiments, die sensor system 300 includes a vibrational element configured to generate haptic alerts.

At block 520, the method 500 includes detecting a change in a parameter that correlates to, and is indicative of, a change in circumference. The sensor system 300 is configured to be worn by the monitored individual over a period of time, for example, from several hours to several weeks. During that time, the inductance, resistance, capacitance, and/or other parameter of the circumference sensor 361 changes as the circumference of the body portion changes. These changes in the parameter of the circumference sensor 361 may be detected, filtered, and processed by the processing unit 330 continuously or repeatedly, for example, at regular intervals.

At block 530, the sensor system 300 obtains a circumference measurement fen the detected change in the parameter. The circumference measurement is calculated by the processing unit 330 using pre-programmed relationships and equations correlating circumference and/or strain to the detected change in a parameter. For example, in some embodiments, strain is calculated using the equation:

$$GF = \frac{\frac{\Delta R}{R}}{\varepsilon},$$

where $\varepsilon$=strain; $\Delta R$=change in resistance; R=initial resistance; and GF=gauge factor, which is a predefined value. Additionally or alternatively, in some embodiments, a cross-sectional area of the body portion may be determined using the equation:

$$R = \rho \frac{L}{A},$$

where R=resistance; $\rho$=the specific resistivity, a predefined value; L=length of the electrical component (e.g., length, of the resistor); and A=the cross-sectional area of the body portion. Circumference can be determined, for example, relying on the above equation and the relationships: Area=$\pi r^2$, and Circumference=$2\pi r$, where r=the radius. From these and/or other pre-programmed equations, a change in circumference can be determined from a change in resistance, inductance, or capacitance. The calculated circumference measurement may be an absolute measurement or a relative measurement providing a change in circumference relative to the baseline or other previous circumference measurement.

The processing unit 330 of various embodiments calculates circumference measurements repeatedly, for example, at regular intervals. In some embodiments, the interval length varies based on the circumference measurements. For example, the processing unit 330 may begin calculating circumference measurements at a first interval (e.g., every hour). When a change in circumference is detected, the processing unit 330 may transition to calculating circumference measurements at a second, more frequent interval (e.g., every 15 minutes) to enable closer monitoring of the circumference. By obtaining circumference measurements frequently over time, the sensor system 300 is able to identify and exclude anomalous measurements, for example, those caused by movement, muscle flexing, or noise.

As shown at block 540, in some embodiments, the sensor system 300 may optionally acquire measurements from one or more additional parameters. For example, one or more of the orientation sensor 362, motion sensor 363, temperature sensor 364, and image sensor 365 may sense changes in one or more parameters, and the changes may be detected, filtered, and processed by the processing unit 330.

As show at block 570, in various embodiments, the antenna 370 of the sensor system 300 transmits the circumference measurements and any other acquired measurements from the processing unit 330 of the sensor system 300 to a mobile computing device 120. In order to successfully transmit the measurements, in some embodiments, the sensor system 300 first determines whether a communication connection exists between the sensor system 300 and the mobile computing device, as shown at block 550. If the sensor system 300 and mobile computing device are not connected, the sensor system 300 stores the measurements and data in memory 340 in the sensor module 320 until a connection is established, as shown at block 560. When a communication connection does exist, the antenna 370 may transmit the measurements and data upon establishing the connection, upon receiving new measurements, at a programmed interval, or when requested by the mobile computing device 120. In some embodiments the mobile computing device 120 receives and analyzes the measurements (as described in more detail below), and based on the measurements, the mobile computing device 120 transmits instructions back to the sensor system 300 instructing the sensor system 300 when and/or what measurements should next be queried, processed, or transmitted.

Mobile Computing Device

Figure 6:
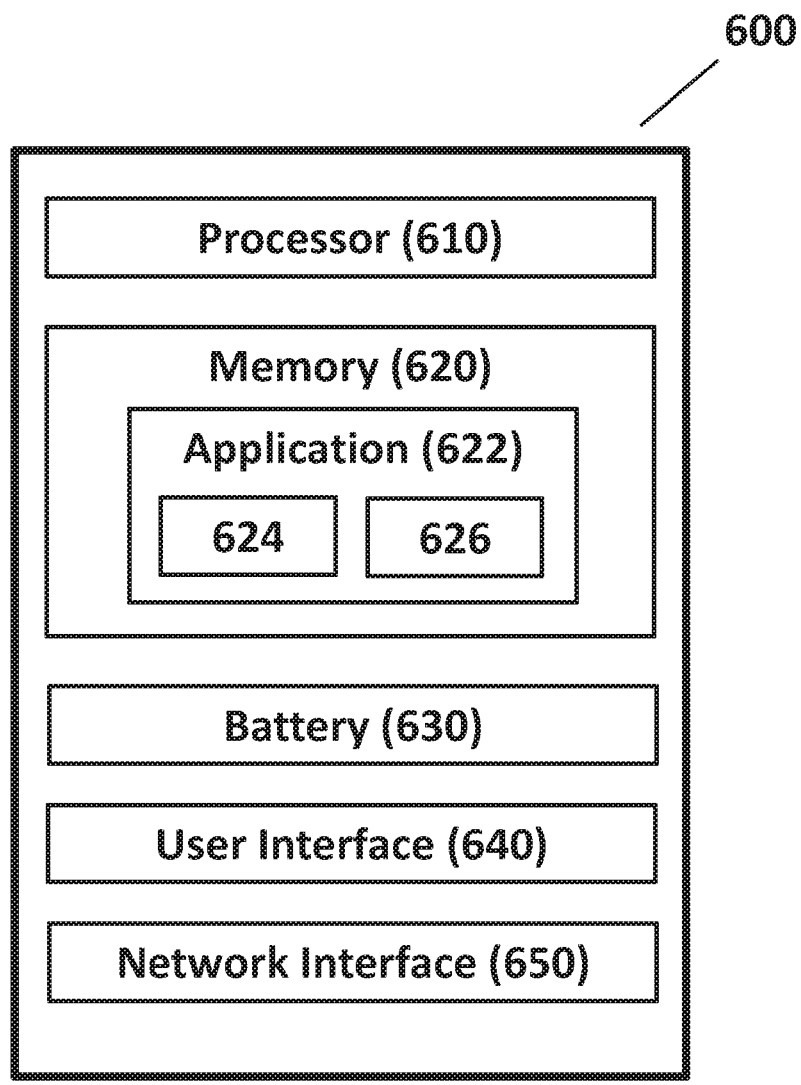
FIG. 6 illustrates a functional block diagram of one embodiment of a mobile computing device provided within the monitoring system of FIG. 1.

FIG. 6 provides a functional block diagram of one embodiment of the mobile computing device. While numbered uniquely, one skilled in the art will appreciate that the mobile computing device 120 of the system 100 may be formed of any embodiment of a mobile computing device described herein and may include any of or all the functional components described with respect to the mobile computing device 600 of FIG. 6. Moreover, although illustrated separately, it is to be appreciated that the various functional blocks of the mobile computing device 600 need not be separate structural elements.

The mobile computing device 600 of various embodiments includes a processor 610, for example, a general purpose microprocessor. The processor 610 is coupled, via one or more buses, to the memory 620 in order to read information from and write information to the memory 620. The memory 620 may be any suitable computer-readable medium that stores computer-readable instructions for execution by computer-executable components. In various embodiments, the computer-readable instructions include software stored in a non-transitory format, some such software having been downloaded as an application 622 onto the memory 620. The processor 610, in conjunction with the software stored in the memory 620, executes an operating system and the application 622. Some methods described elsewhere herein may be programmed as software instructions contained within the application 622 stored in the memory 620 and executable by the processor 610.

In various embodiments, a power supply, such as a battery 630 is included within the mobile computing device 600 and is electrically coupled to provide power to the processor 610 and other electronic components. The battery 630 may be rechargeable or disposable.

The mobile computing device 600 of various embodiments includes a plurality of interfaces, such as a user interface 640 and a wireless network interface 650. The user interface 640 may include one or more input/output (I/O) devices. In some embodiments, the user input device includes one or more of a button, switch, touchscreen, and keyboard, and the output device includes one or more of a display screen, light display, audio output, and haptic output. The wireless network interface 650 of some embodiments includes a receiver and transmitter for bi-directional communication. The receiver receives and demodulates data received over a communication network. The transmitter prepares data according to one or more network standards and transmits data over a communication network. A communication antenna in the form of a transceiver may act as both a receiver and a transmitter. In some embodiments, the mobile computing device 600 includes a plurality of network interfaces 650, including a first network interface configured for communication with the sensor system 300 and a second network interface configured for communication with a network computing device 130.

In various embodiments, a health monitoring application 622 is downloaded from a network computing device 130 onto the mobile computing device 600 by the monitored individual. The health monitoring application 622 may include one or more of a user interaction module 624 and a data processing module 626.

The user interaction module 624 of various embodiments instructs the mobile computing device 600 to request information from, and provide information to, the monitored individual. The user interaction module 624 includes a graphical user interface displayable on a screen through which the monitored individual can interact with the monitoring system. The monitored individual may also interact with the user interaction module 624 through audio and/or verbal inputs and outputs. For example, in some embodiments, the user interaction module 624 generates sounds through which the monitoring system can provide instructions and/or information to a monitored individual and query the monitored individual for information. In some embodiments, voice recognition capabilities allow a monitored individual to verbally respond to requests for information.

One non-limiting example of a graphical user interface generated by the user interaction module 624 is provided in FIG. 7A. As shown at FIG. 7A, in various embodiments of the monitoring system, upon downloading the health monitoring application 622 onto a mobile computing device 600, a login screen prompts the monitored individual for login, credentials, including, for example, a username and password. The monitoring system 100 of various embodiments is configured to be secure, requiring every user of the system (e.g., including monitored individuals, supervisors, reviewers, and system administrators) to enter proper login credentials demonstrating authorization to use the system prior to interacting with the monitoring system. Following the initial download of, and log in to, the health monitoring application 622, the mobile computing device 600 may perform a method to search for, and communicatively pair with, a nearby sensor system 300. In future uses of the system, the mobile computing device 600 may automatically pair with the same sensor system 300 with which it previously communicated and may allow a monitored individual to provide and receive information related to data being acquired from the specific paired sensor system 300.

In some embodiments, upon logging into the health monitoring application 622 for the first time, the monitored individual is prompted to provide biographical information and/or a medical history. For example, the user interaction module 624 may prompt the monitored individual to enter one or more of a: name, identification code, gender, sex, date of birth, ethnicity, race, height, weight, and medications and/or supplements routinely taken. The information requested by the user interaction module 624 varies depending on the intended use of the monitoring system. For example, in some embodiments, the monitoring system is used for wellness purposes to track changes in circumference of a body portion caused by changes in weight, muscle mass, and/or fetal development. Depending on the intended use, the user interaction module 624 may modify its prompts, for example, in order to request that the monitored individual enter one or more of the following when relevant: desired fitness goals, desired weight loss or weight gain goals, current level of fitness, average amount of exercise performed, gestation age, etc. In other embodiments, the monitoring system is used for healthcare purposes to monitor for changes in circumference of a body portion caused by abnormal swelling. If the monitoring system was prescribed to an individual for use before or following surgery, the user interaction module 624 may request that the monitored individual enter information on the type of surgery and the date of surgery. Additionally or alternatively, in some embodiments, the user interaction module 624 generates prompts requesting that the monitored individual enter in risk factor data relevant to assessing the likelihood that the monitored individual will develop abnormal swelling of the body portion. In some embodiments, the user interaction module 624 requests that the monitored individual select any clinically-relevant risk factors that apply to the individual. The risk factors may be presented in a list and may include, for example, one or more of: paralysis, paresis, plaster immobilization of a limb, active cancer and stage of cancer malignancy and treatment, previous history of deep vein thrombosis (DVT) and/or pulmonary embolism (PE), family history of DVT and/or PE, obesity, history of smoking, heart disease, lung disease, inflammatory bowel disease, recent childbirth, pregnancy, blood clotting disorder, advanced age (e.g., over 70 years of age), and/or use of supplemental estrogen or birth control pills.

Additionally or alternatively, in some embodiments of the monitoring system, the user interaction module 624 prompts the monitored individual to enter in information related to a current health or wellness status and/or current or recent habits and activities. For example, the user interaction module 624 may request that the monitored individual enter in information related to one or more of: symptoms, a wellness rating, a pain rating, an exercise performed, a food consumed, a supplement consumed, a medication administered, a duration of sleep attained, and an indication of whether the monitored individual has complied with a prescribed instruction. The user interaction module 624 may prompt the monitored individual for such information on a regular basis (e.g., daily or hourly), upon each opening of the health application 622 on the mobile computing device 600, or upon detection of a change in status (e.g., a change in a circumference measurement reading or a change in acceleration).

As shown in the non-limiting graphical user interfaces provided in FIGS. 7B-7C, the user interaction module 624 is also configured to provide information to a monitored individual. For example, the user interaction module 624 may enable the monitored individual to review his or her previously-entered medical history, current or recent measurements acquired from the sensor system, a history of the tracked measurements acquired from the sensor system (as shown in FIG. 7B), and/or health or wellness information. In some embodiments, the user interaction module 624 provides the monitored individual with access to a library of health and wellness information, for example, to a library of information maintained by a third party provider, such as WebMD® or the Mayo Clinic® (as shown in FIG. 7C). In some embodiments, the user interaction module 624 provides the monitored individual with access to individual-specific instructions customized by the monitored individual's health or wellness professional (i.e., supervisor). The individual-specific instructions may include pre-operative instructions, post-operative instructions, instructions related to a diet or exercise regimen, or any other instructions the supervisor chooses to share with the monitored individual. The instructions may include, for example, notifications of suggested meals or exercises or reminders to sleep, exercise, elevate the legs, limit exertion, or take medications or supplements. In some embodiments, the user interaction module 624 provides the monitored individual with access to instructional videos, for example, videos demonstrating how to perform recommended or prescribed exercises or how to cook various recommended healthy meals.

In various embodiments, the user interaction module 624 also provides information to the monitored individual in the form of alert outputs. The alert outputs may be generated at a regular interval or upon detection of a change in circumference or other monitored health parameter. The alert outputs may include notes of encouragement, notifications of progress, reminders of particularly relevant instructions, or an instruction to contact a healthcare provider. Three non-limiting examples of graphical user interfaces displaying alert outputs are provided in FIGS. 7D-7F. In each of FIGS. 7D-7F, the alert output includes a numerical and pictorial indication of progress and a message providing pertinent feedback. Additional users of the monitoring system, for example, supervisors and/or reviewers, may also be able to transmit messages to the monitored individual through the system, which are displayable in the graphical user interface of the user interaction module 624.

The information requested front, and provided to, the monitored individual is customizable based on the intended use of the monitoring system. In some embodiments, it is customizable by a system administrator. Additionally or alternatively, in some embodiments, it is customizable by a healthcare provider, athletic coach, personal trainer, or other health or wellness supervisor.

Figure 8:
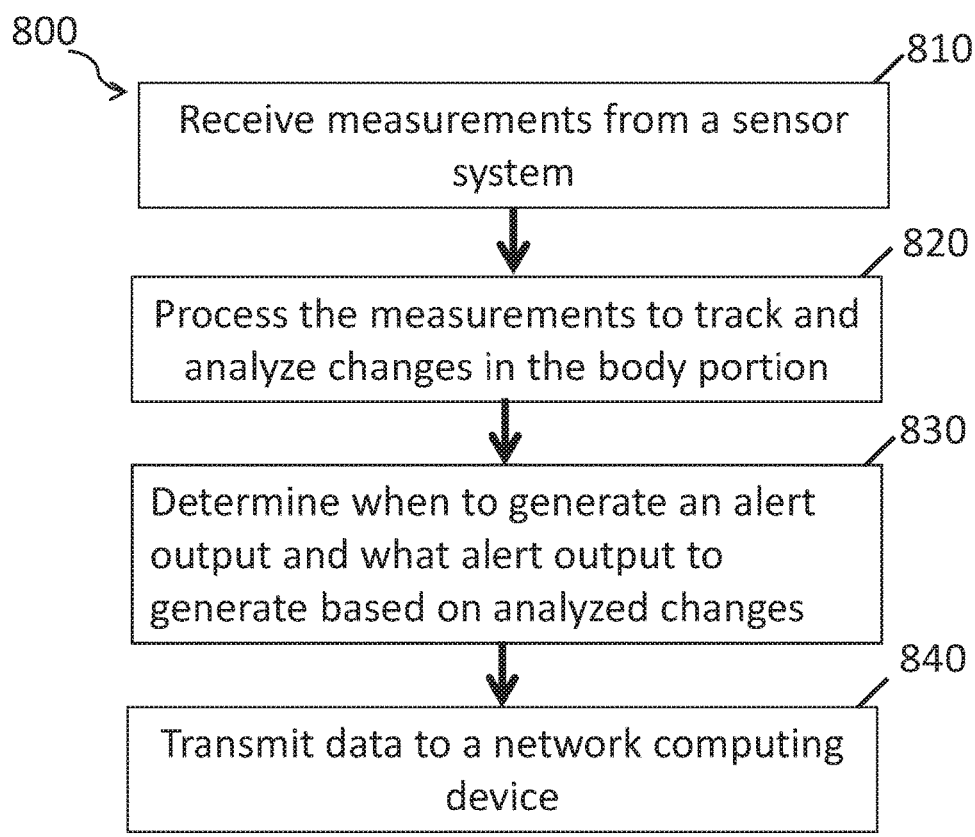
FIG. 8 illustrates a flow chart of one embodiment of a method performed by the mobile computing device of FIG. 6.

The health application 622 of various embodiments also includes a data processing module 626. The date processing module 626 includes the software that instructs the mobile computing device 600 to perform various data processing methods. One method directed by the software of the data processing module 626 is depicted in FIG. 8. As shown at block 810 of the depicted method, the mobile computing device 600 receives measurements from the sensor system 300. As described above, these measurements may be relative or absolute measurements. The measurements include circumference measurements of the body portion or measurements indicative of circumference. In some embodiments, the raw measurements (such as measurements of changes in resistance, capacitance, or inductance) are received by the mobile computing device 600 from the sensor system 300 and processed by the mobile computing device 600 to determine circumference. Additionally, the measurements may optionally include one or more additional measurements of health parameters such as orientation, acceleration, skin temperature, skin color, and/or cardiovascular performance (e.g., blood oxygenation, blood volume, pulse rate, or heart rate). At block 820, with the aid of the data processing module 626, the mobile computing device 600 processes the received measurements to track and analyze changes in the body portion. Additionally, the mobile computing device 600 determines when to generate an alert output and what alert output to generate based on any analyzed changes to the body portion, as shown at block 830. The mobile computing device also transmits data, including the received measurements, the analysis of measurements, and data received via user inputs, to a network computing device, as shown at block 840.

In some embodiments, processing the received measurements to track and analyze changes in the body portion involves assigning a relative weight to one or more measured parameters of importance and calculating an overall score from the weighted measurements. The overall score may be an overall risk score or wellness score. In some embodiments, the overall score corresponds to a likelihood of onset of a disease that causes abnormal swelling of a limb. For example, the overall score may correspond to the likelihood that the monitored individual has developed interstitial edema, deep vein thrombosis, pulmonary embolism, lymphedema, or other medical condition (e.g., congestive heart failure, liver disease, kidney disease, an allergic reaction, or inflammation from injury or infection) that causes abnormal swelling. As another example, the overall score may correspond to a monitored individual's level of success in improving overall wellness. Such a score may be applicable, for example, when the monitoring system is being used to track gradual circumferential changes of a body portion, for example those associated with weight gain, weight loss, a growing fetus, or an increase in muscle mass. Such a system may be used, for example, by individuals who are overweight, underweight, being treated for cancer, pregnant, or athletes. One, some, or all of the measured parameters may contribute to the overall score, including one or more of: the change in circumference of the body portion, a skin temperature at the body portion, a skin color at the body portion, and movement of the body portion. Additionally, one or more user inputs and/or a compliance score may contribute to the overall score.

In some embodiments, the compliance score is also calculated by the mobile computing device 600 using the software of the data processing module 620. The compliance score is an indication of the degree to which the monitored individual complied with prescribed instructions. The compliance score may be calculated based on one or more of: the change in circumference of the body portion, the user inputs, detected motion of the body portion indicative of an exercise, and a detected orientation of the body portion. For example, if the prescribed instructions include an instruction to upwardly tilt or elevate the legs, the compliance score may be determined, at least in part by monitoring leg orientation. If the prescribed instructions include an instruction to perform leg exercises, the compliance score may be determined, at least in part, by monitoring leg movement. If the prescribed instructions include an instruction to administer a medication, the compliance score may be determined, at least in part, from a user-entered input indicating medication administration.

In some embodiments, an alert output is generated when the overall score exceeds a predefined threshold. In some embodiments, an alert output is generated when a compliance score falls below a predefined threshold. In some embodiments, an alert output reporting progress is generated following every receipt of a parameter measurement. In some embodiments, a supervisor can configure when an alert output is generated. In some embodiments, the alert output is a visual or audible alert presented by the mobile computing device 600. Additionally or alternatively, the alert output may be a message that is transmitted to another communicatively connected device, such as a supervisor computing device or a reviewer computing device.

Figure 9:
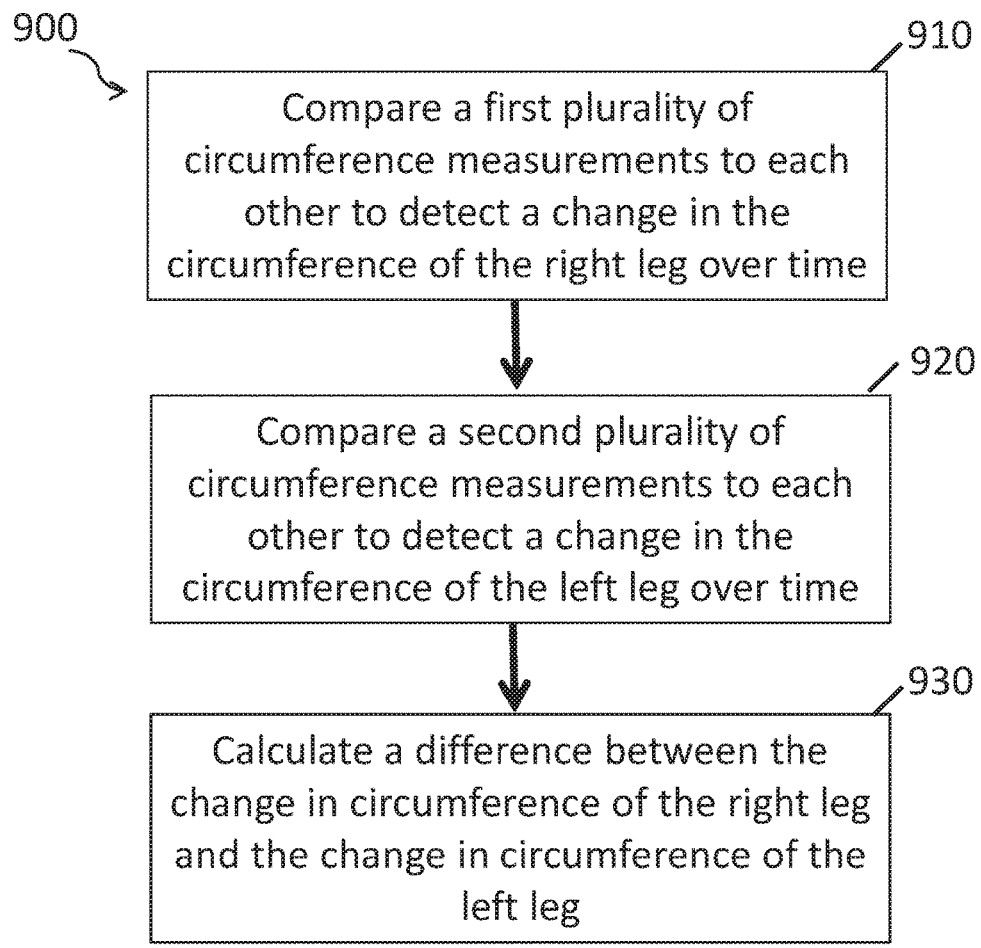
FIG. 9 illustrates a flow chart of another embodiment of a method performed by the mobile computing device of FIG. 6.

In some embodiments, the specific data analysis functions performed by the mobile computing device 600 are customized based on the intended use/purpose of the monitoring system. One example of a specialized method of data analysis performed by the mobile computing device 600 is provided in FIG. 9. In the illustrated example, the mobile computing device 600 is communicatively coupled to a sensor system 300 formed of at least two stretchable components and two sensor modules. A first stretchable component with a first sensor module is positioned on the right leg of the monitored individual and configured to obtain a first set of parameter measurements, including a first set of circumference measurements. A second stretchable component with a second sensor module is positioned on the left leg of the monitored individual and configured to obtain a second set of parameter measurements, including a second set of circumference measurements, in the illustrated embodiment, processing the parameter measurements to track and analyze changes includes: comparing the first plurality of circumference measurements to each other to detect a change in the circumference of the right leg over time, as shown at block 910; comparing the second plurality of circumference measurements to each other to detect a change in the circumference of the left leg over time, as shown at block 920; and calculating a difference between the change in circumference of the right leg and the change in circumference of the left leg, as shown at block 930. The difference between the change in circumference of the right leg and the change in circumference of the left leg may contribute to a determination of the appropriate timing or content of the alert output. For example, in some embodiments, an alert output may be generated when the difference between the change in circumference of the right leg and the change in circumference of the left leg exceeds a threshold value.

Additionally, in some embodiments, the specific data analysis functions performed by the mobile computing device 600 may be further customizable for each monitored individual. In some embodiments, the analysis functions stored in software of the data processing module 626 are modifiable by system administrators and/or health and wellness professionals via interaction with an analytics system stored on a network computing device.

Analytics System

Figure 10:
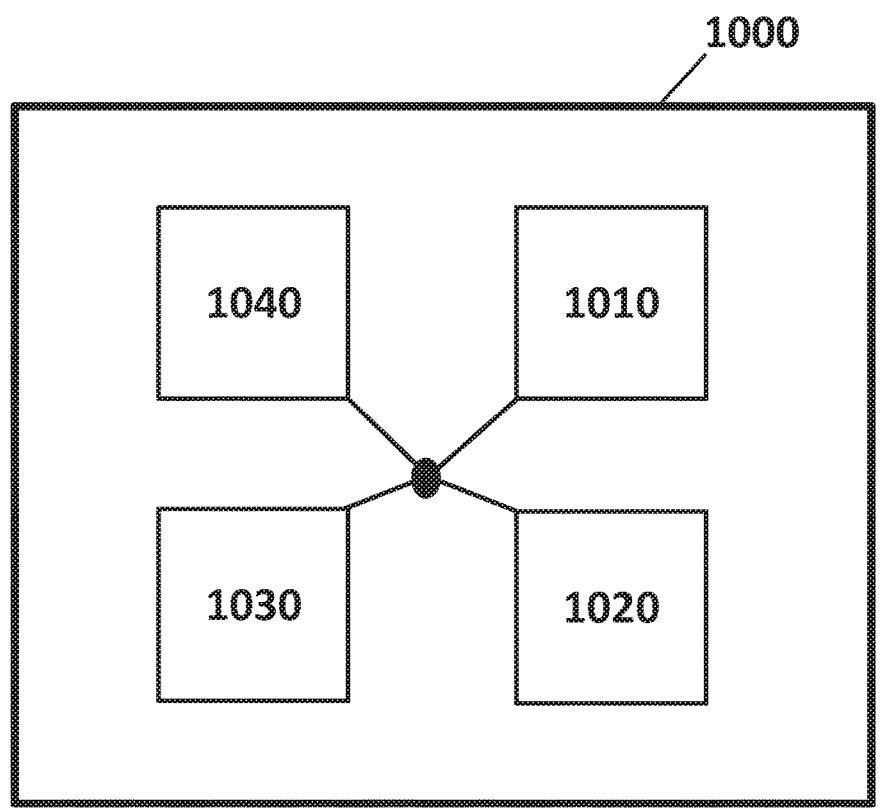
FIG. 10 illustrates a schematic block diagram of one embodiment of a network computing device provided within the monitoring system of FIG. 1.

A schematic block diagram of the analytics system is illustrated in FIG. 10. The analytics system 1000 is stored on the network computing device 130 introduced in FIG. 1. The analytics system refers to the backend system of the overall monitoring system. The analytics system 1000 includes a monitored-individual module 1010, a supervisor module 1020, a reviewer module 1030, and an administrator module 1040 through which each user of the monitoring system can interact with the network computing device 130.

The monitored-individual module 1010 stores all user data related to the monitored individual, including login credentials, medical history, a record of symptoms, and/or other user-entered information, and a log of parameter measurements and related analyses. It also stores all instructions that are transmitted to and downloadable by the mobile computing device 600. These include application instructions (i.e., software) and prescribed health-related instructions intended for the monitored individual. The monitored-individual module 1010 of some embodiments is also configured to perform additional analytics of the monitored individual's data and/or population-wide data. It will also be appreciated by those of skill in the art that, in some embodiments, some of or all the data analysis functions that were described above as being performed by the mobile computing device 600 may additionally or alternatively be performed by the analytics system 1000 of the network computing device.

The supervisor module 1020 hosts or stores the software for an application-based or web-based super visor portal which a supervisor can access using a supervisor computing device. Through the portal a health or wellness professional can log into the monitoring system and review parameter measurements, data analyses, and alters pet taming to one monitored individual and/or an entire population of monitored individuals. In some embodiments, the portal enables a health or wellness professional to view trends, averages, charts, and other displays of population-wide data pertaining to a plurality of their patients, clients, or athletes. The supervisor module 1020 may also enable the supervisor to configure and modify alert algorithms, which the monitoring system uses to determine when to generate alerts for the monitored individual and what alerts to generate. For example, a supervisor may be able to select which parameters to include in an overall score calculation and/or what weighting to assign each parameter. Through the supervisor portal, a health or wellness professional can also create, customize, and or modify prescribed instructions for the monitored individual, and select specific parameters for the sensor system to monitor. The supervisor may also be able to select or compose messages for transmission to the mobile computing device of the monitored individual.

The reviewer module 1030 hosts or stores the software for an application-based or web-based reviewer portal, which a reviewer can access using a reviewer computing device. Through the portal, a reviewer can log into the monitoring system and review parameter measurements, data analyses, and alerts pertaining to a monitored individual. In some embodiments, the monitored individual may be able to control which information is shared with and viewable by a reviewer. In some embodiments, the reviewer module enables the reviewer to select or compose messages for transmission to the mobile computing device 120 of the monitored individual and/or the supervisor computing device 140.

The administrator module 1040 includes the software that enables user authentication of a system administrator. Upon logging into the system, the system administrator may be able to access, and optionally, modify, some of or all the software that forms the analytics system.

The analytics system 1000 connects ail the users of the system together, enabling the transmission of information between one or more mobile computing devices, one or more supervisor computing de vices, one or more reviewer computing devices, and/or one or more administrator computing devices.

In various embodiments, the network computing device, the supervisor computing devices, the reviewer computing devices, and the administrator computing devices each includes some of or all the functional components described above in relation to the mobile computing device 200 of FIG. 2, but with different software loaded thereon. For example, each device includes a processor and memory having instructions stored thereon, wherein execution of the instructions by the processor, cause the processor to perform various methods. Moreover, each of the computing devices includes a network interface for receiving and transmitting data, and each computing device may include or be coupled to an input device for receiving user inputs and an output device for conveying information.

The examples and illustrations included herein show, by way of illustration and not of limitation, specific embodiments in which the subject matter may be practiced. Other embodiments may be utilized and derived therefrom, such that modifications may be made without departing from the scope of this disclosure. This disclosure is intended to cover any and all adaptations or variations of various embodiments, and it will be readily apparent to those of ordinary skill in the art, in light of the teachings of these embodiments, that numerous changes and modifications may be made without departing from the spirit or scope of the appended claims.

What is claimed is:

1. A monitoring system for detecting circumferential changes to a portion of a body, the monitoring system comprising:
    a sensor system wearable around a portion of an individual's body and configured to obtain and transmit measurements for a plurality of parameters of the body portion over a period of time, the plurality of parameters including a circumference of the body portion and one or more of a surface skin temperature, an orientation of the body portion, an acceleration of the body portion, and a color of a surface of the body portion;
    a mobile computing device comprising a processor and a non-transitory computer-readable medium with instructions stored thereon, wherein the instructions, when executed by the processor, cause the processor to perform a method comprising:
        receiving the measurements for the plurality of parameters,
        applying relative weights to the plurality of parameters to generate weighted measurements,
        calculating an overall score based on the weighted measurements and one or more additional factors, the one or more additional factors comprising one or more of a compliance score and a user input entered by the individual, and
        generating an alert output when the overall score exceeds a predefined threshold; and
    a supervisor computing device communicatively coupled to the mobile computing device, wherein the supervisor computing device is configured to receive inputs from a professional, and transmit instructions to the mobile computing device, specifying which plurality of parameters and additional factors to include in the overall score.

2. The monitoring system of claim 1, wherein the instructions stored on the computer-readable medium further cause the processor to query the individual for the user input.

3. The monitoring system of claim 2, wherein the user input comprises one or more of symptoms and risk factor data.

4. The monitoring system of claim 2, wherein the user input comprises data inputs related to one or more of: an exercise performed, a food consumed, a supplement consumed, a medication administered, a duration of sleep, and a daily wellness rating.

5. The monitoring system of claim 2, wherein the user input comprises an indication of whether the individual has complied with a prescribed instruction.

6. The monitoring system of claim 2, wherein the instructions stored on the computer-readable medium further cause the processor to:
    calculate a change in circumference of the body portion,
    compute the compliance score from the change in circumference and the user input, and
    transmit the compliance score to a network computing device.

7. The monitoring system of claim 1, wherein the sensor system comprises a stretchable component and a sensor module coupled thereto, the stretchable component being configured to fit securely around the body portion.

8. The monitoring system of claim 7, wherein the stretchable component comprises a stretchable band, sleeve, belt, brace, or garment.

9. The monitoring system of claim 7, wherein the sensor module comprises a strain gauge configured to detect a force caused by stretching the stretchable component, and wherein the force correlates to a circumference measurement.

10. The monitoring system of claim 7, wherein the sensor module comprises: an electrical component configured to change inductance when the stretchable component is stretched, and a sensor configured to detect the change in inductance, the change in inductance being indicative of a change in circumference.

11. The monitoring system of claim 7, wherein the sensor module comprises: an electrical component configured to change resistance when the stretchable component is stretched, and a sensor configured to detect the change in resistance, the change in resistance being indicative of a change in circumference.

12. The monitoring system of claim 7, wherein the sensor module comprises: an electrical component configured to change capacitance when the stretchable component is stretched, and a sensor configured to detect the change in capacitance, the change in capacitance being indicative of a change in circumference.

13. The monitoring system of claim 1, wherein at least some of the measurements for the plurality of parameters are relative measurements benchmarked to a baseline or previous parameter reading.

14. The monitoring system of claim 1, wherein the body portion comprises a limb, upper torso, or lower torso.

15. The monitoring system of claim 1, wherein the body portion comprises a right leg and a left leg of the individual, and wherein the sensor system comprises: a first component configured to obtain a first plurality of circumference measurements over time from a fixed location on the right leg, and a second component configured to obtain a second plurality of circumference measurements over time from an equivalent fixed location on the left leg.

16. The monitoring system of claim 15, further comprising processing the measurements for the plurality of parameters including a measurement for circumference, wherein processing the measurement for circumference comprises:
    comparing the first plurality of circumference measurements to detect a change in the circumference of the right leg over time,
    comparing the second plurality of circumference measurements to detect a change in the circumference of the left leg over time, and
    calculating a difference between the change in circumference of the right leg and the change in circumference of the left leg.

17. The monitoring system of claim 16, wherein applying relative weights to the plurality of parameters comprises applying a relative weight to the difference between the change in circumference of the right leg and the change in circumference of the left leg.

18. The monitoring system of claim 1, wherein the compliance score is an indication of a level of compliance by the individual with prescribed instructions, and wherein the compliance score is determined from one or more of: a detected leg orientation, a detected leg movement, and a user-entered input related to compliance.

19. The monitoring system of claim 18, wherein the prescribed instructions comprise one or more of instructions to elevate a leg, instructions to perform an exercise, and instructions to take a medication.

20. The monitoring system of claim 18, wherein the prescribed instructions are customizable by the professional using the supervisor computing device.

21. The monitoring system of claim 1, wherein the alert output is generated if the mobile computing device detects a possible onset of a disease that causes abnormal swelling of the body portion.

22. The monitoring system of claim 21, wherein the disease that causes abnormal swelling of the body portion is interstitial edema, deep vein thrombosis, pulmonary embolism, or lymphedema.

23. The monitoring system of claim 1, wherein the alert output comprises an instruction to the individual to consult a healthcare provider for evaluation.

24. The monitoring system of claim 1, wherein the alert output comprises an evaluation of strength training effectiveness or progress.

25. The monitoring system of claim 1, wherein the sensor system comprises one or more of: a temperature sensor, a gyroscope, an accelerometer, and an image sensor.

26. The monitoring system of claim 1, further comprising a network computing device communicatively coupled to the mobile computing device and configured to receive and store the measurements for the plurality of parameters, generate and transmit alerts to an authorized user, and store and transmit instructions to the mobile computing device.

27. The monitoring system of claim 7, wherein the sensor module comprises electronics configured such that at least one of the following occurs: the sensor module automatically activates upon attachment to the stretchable component, and the sensor module automatically deactivates upon detachment from the stretchable component.

28. The monitoring system of claim 7, wherein the sensor module comprises electronics configured to perform an initial status check following placement of the sensor system around the body portion, the initial status check comprising: detecting an amount of strain in the stretchable component, determining whether the amount of strain exceeds a safety threshold, and generating an alert at the sensor system to indicate that the stretchable component is too tight if the safety threshold is exceeded.

29. The monitoring system of claim 1, wherein the supervisor computing device is further configured to receive inputs from the professional and transmit instructions to the mobile computing device specifying the relative weights to apply to the plurality of parameters.

* * * * *